US009131791B2

(12) United States Patent
Schwingendorf et al.

(10) Patent No.: US 9,131,791 B2
(45) Date of Patent: Sep. 15, 2015

(54) SLEEPY HEADS NECK PILLOW

(71) Applicants: Alice Jean Schwingendorf, Tokyo (JP); Gabriel Olivier Durand, Tokyo (JP)

(72) Inventors: Alice Jean Schwingendorf, Tokyo (JP); Gabriel Olivier Durand, Tokyo (JP)

( * ) Notice: Subject to any disclaimer, the term of this patent is extended or adjusted under 35 U.S.C. 154(b) by 0 days.

(21) Appl. No.: 14/669,423

(22) Filed: Mar. 26, 2015

(65) Prior Publication Data

US 2015/0216335 A1 Aug. 6, 2015

Related U.S. Application Data

(60) Division of application No. 13/240,095, filed on Sep. 22, 2011, now Pat. No. 9,021,636, which is a continuation-in-part of application No. 12/659,814, filed on Mar. 22, 2010, now Pat. No. 8,141,187.

(51) Int. Cl.
*A47G 9/10* (2006.01)
*B60N 2/48* (2006.01)

(52) U.S. Cl.
CPC ............ *A47G 9/1009* (2013.01); *A47G 9/1081* (2013.01); *B60N 2/48* (2013.01)

(58) Field of Classification Search
CPC .................. A47G 9/10; A47G 9/1009; A47G 2009/1018; A47G 9/1081; A47G 9/109; A47C 7/38; A47C 7/383; B60N 2/48; B60N 2/4802; B60N 2/4805; B60N 2/4808; B60N 2/4832; B60N 2/487; B60N 2/4879; B60N 2/4882
USPC ............... 5/636, 637, 640, 643; 297/393, 397
See application file for complete search history.

(56) References Cited

U.S. PATENT DOCUMENTS

| | | | |
|---|---|---|---|
| 1,510,187 | A | 9/1924 | Martin |
| 1,579,585 | A | 4/1926 | Wieder et al. |
| 2,638,152 | A | 5/1953 | Pulsifer |
| 3,029,107 | A | 4/1962 | Myers |
| 3,285,658 | A | 11/1966 | Cleveland |
| 4,285,081 | A | 8/1981 | Price |
| 4,345,347 | A | 8/1982 | Kantor |
| 4,562,833 | A | 1/1986 | Pujals, Jr. |
| 4,617,691 | A | 10/1986 | Monti et al. |
| 4,708,129 | A | 11/1987 | Pujals, Jr. |
| 4,738,488 | A | 4/1988 | Camelio |

(Continued)

FOREIGN PATENT DOCUMENTS

| | | |
|---|---|---|
| AU | 8872501 A | 4/2002 |
| CN | 101166446 A | 4/2008 |

(Continued)

OTHER PUBLICATIONS

International Search Report mailed Apr. 26, 2011 in co-pending PCT application No. PCT/JP2011/000779.

(Continued)

*Primary Examiner* — Robert G Santos
(74) *Attorney, Agent, or Firm* — Nields, Lemack & Frame, LLC

(57) ABSTRACT

The embodiments disclosed herein are related to a supportive head and neck pillow with a supportive bone structure inside the pillow. The pillow is used for head and neck support, and comfort while sleeping sitting up during transportation. It can also be used for head and neck support for people who have neck injuries, or to prevent neck injuries during transportation. The sleepy heads neck pillow disclosed comprises a pillow with a bone structure support inside it.

4 Claims, 30 Drawing Sheets

(56) References Cited

U.S. PATENT DOCUMENTS

| | | |
|---|---|---|
| 4,815,154 A | 3/1989 | Grimes |
| D334,159 S | 3/1993 | Mulligan |
| 5,505,523 A | 4/1996 | Wang |
| 5,778,469 A | 7/1998 | Festa |
| D396,594 S | 8/1998 | Lefebvre |
| 5,868,471 A | 2/1999 | Graham et al. |
| 5,974,607 A | 11/1999 | Smith |
| D420,845 S | 2/2000 | Rumage |
| 6,123,389 A | 9/2000 | O'Connor et al. |
| 6,305,749 B1 | 10/2001 | O'Connor et al. |
| 6,786,554 B1 | 9/2004 | Zahiri |
| D503,062 S | 3/2005 | Nash |
| 6,893,094 B2 | 5/2005 | O'Connor |
| D522,300 S | 6/2006 | Roberts |
| D531,424 S | 11/2006 | Kusachi |
| 7,197,781 B2 | 4/2007 | Ramsbottom et al. |
| 7,204,557 B1 | 4/2007 | Burton |
| 7,393,057 B2 | 7/2008 | Fraser |
| 7,547,071 B2 | 6/2009 | Huffman |
| 7,644,990 B2 | 1/2010 | Pearson |
| D619,402 S | 7/2010 | Sternlight et al. |
| 7,908,692 B2 | 3/2011 | Lange |
| 8,141,187 B2 | 3/2012 | Schwingendorf et al. |
| D664,799 S | 8/2012 | Schwingendorf et al. |
| D665,212 S | 8/2012 | Schwingendorf et al. |
| 8,418,293 B2 | 4/2013 | Tansingco |
| 8,646,135 B2 | 2/2014 | Shamaiengar |
| 8,650,684 B1 | 2/2014 | Mackinnon |
| 8,863,335 B2 | 10/2014 | Shamaiengar |
| 8,898,840 B1 | 12/2014 | Majette |
| 9,021,636 B2 | 5/2015 | Schwingendorf et al. |
| 2001/0049844 A1 | 12/2001 | Gilbert |
| 2001/0054837 A1 | 12/2001 | O'Connor |
| 2005/0102758 A1 | 5/2005 | Ramsbottom et al. |
| 2005/0179300 A1 | 8/2005 | O'Connor et al. |
| 2006/0244300 A1 | 11/2006 | Watson Savage |
| 2007/0056107 A1 | 3/2007 | Gabriel |
| 2011/0094035 A1 | 4/2011 | Tansingco |
| 2011/0225736 A1 | 9/2011 | Schwingendorf et al. |
| 2012/0011655 A1 | 1/2012 | Rojas |
| 2012/0030876 A1 | 2/2012 | Schwingendorf et al. |
| 2013/0047342 A1 | 2/2013 | Schwingendorf et al. |
| 2013/0333117 A1 | 12/2013 | Shamaiengar |
| 2014/0115788 A1 | 5/2014 | Shamaiengar |
| 2015/0157130 A1* | 6/2015 | Kellock et al. ............ A47C 7/38 |

FOREIGN PATENT DOCUMENTS

| | | |
|---|---|---|
| DE | 10196653 B | 12/2005 |
| GB | 2382985 A | 6/2003 |
| GB | 2382985 B | 4/2005 |
| JP | 2-80045 A | 3/1990 |
| JP | 3015207 U | 8/1995 |
| JP | 3024929 U | 6/1996 |
| JP | 2000-232928 A | 8/2000 |
| JP | 2002-325656 A | 11/2002 |
| JP | 2005-95472 A | 4/2005 |
| JP | D1455503 S | 10/2012 |
| WO | 02/24031 A1 | 3/2002 |
| WO | 2011/118120 A1 | 9/2011 |
| WO | 2013/042365 A1 | 3/2013 |

OTHER PUBLICATIONS

Written Opinion mailed Apr. 26, 2011 in co-pending PCT application No. PCT/JP2011/000779.

International Preliminary Report on Patentability mailed Oct. 4, 2012 in co-pending PCT application No. PCT/JP2011/000779.

International Search Report and Written Opinion mailed Dec. 25, 2012 in co-pending PCT application No. PCT/JP2012/005980.

Chinese communication, with English translation, issued Sep. 9, 2013 in co-pending Chinese patent application No. CN 201180015188.1.

Office Action mailed Aug. 6, 2014 in co-pending U.S. Appl. No. 13/635,776.

Final Rejection mailed Feb. 11, 2015 in co-pending U.S. Appl. No. 13/635,776.

* cited by examiner

SLEEPY HEADS NECK PILLOW

This application is a divisional of Ser. No. 13/240,095, filed Sep. 22, 2011, now U.S. Pat. No. 9,021,636, which is a continuation-in-part of Ser. No. 12/659,814, filed Mar. 22, 2010, now U.S. Pat. No. 8,141,187, the disclosures of which are incorporated herein by reference.

FIELD OF THE INVENTION

The invention is a supportive head neck pillow with a supportive bone structure inside the pillow. The invention is used for head and neck support, and comfort while sleeping sitting up during transportation.

BACKGROUND OF THE INVENTION

The reason we thought about this invention is because like us, and millions of other people can't sleep comfortably when sitting up during traveling (airplane, train, bus trip, and passenger in cars, etc.). Another reason we thought about this invention is because it is suitable for people who have neck injuries, it will help keep their head and neck secure during traveling (airplane, train, bus trip, and passenger in cars, etc.). It will also procure a great feeling of comfort. After research and testing many different heads neck pillows on the market, not one was satisfactory to give the support, and comfort while sitting up sleeping. We decided to invent a head neck pillow that would have a great comfort, and with inside the pillow have a supportive bone structure that will conform, fit the shape of the neck with great support.

SUMMARY OF THE INVENTION

The sleepy heads neck pillow of the present invention is a new style supportive pillow that will give your neck, head and upper back support. It will give great comfort while sleeping while sitting up during transportation.

The invention is related to a supportive heads neck pillow with a supportive bone structure inside the pillow. The invention is used for head and neck support, and comfort while sleeping sitting up during transportation. It can also be used for head and neck support for people who have neck injuries, or to prevent neck injuries during transportation. The sleepy heads neck pillow of the invention comprises a pillow with a bone structure support inside it, which gives support and comfort to the head, neck, and upper back. The sleepy heads neck pillow of the invention optionally comprises supportive, adjustable straps which are connected to the adjustable clips which give the extra support to the pillow when connected to a seat.

That is, the invention has the following constitutions:
(1) A sleepy heads neck pillow, comprising a pillow with a bone structure support inside the pillow, wherein the bone structure support is fully incased in the pillow, and the bone structure support comprises two parts; a neck bone support having a top edge, a bottom edge, a left edge and a right edge, wherein the neck bone support is configured to conform to and support the back of the neck of the user, and one or two or more arm bone supports respectively extending from the left and/or right edges of the neck bone support, wherein a length of each arm bone is substantially greater than a width of each arm bone support so that the arm bone supports are configured to extend forwardly of the shoulders of the user to support the user's head when the head is resting to the side, and, and the bone structure support is made of one piece.

(2) The sleepy heads neck pillow according to (1), wherein the bone structure support further comprises an upper back bone support that is extended down at an angle from the bottom edge of the neck bone support so that the upper back bone support is configured to give extra support to the neck and upper back of the user.

(3) The sleepy heads neck pillow according to (1) or (2), wherein the bone structure support is adjustable.

(4) A method of donning a sleepy heads neck pillow on a wearer, said sleepy heads neck pillow comprising a pillow with a bone structure support inside the pillow, wherein the bone structure support is fully incased in the pillow, and the bone structure support comprises two parts; a neck bone support having a top edge, a bottom edge, a left edge and a right edge, wherein the neck bone support is configured to conform to and support the back of the neck of the user, and one or two or more arm bone supports respectively extending from the left and/or right edges of the neck bone support and defining a gap between them, wherein a length of each arm bone is substantially greater than a width of each arm bone support so that the arm bone supports are configured to extend forwardly of the shoulders of the user to support the user's head when the head is resting to the side, and, the bone structure support is made of one piece; said method comprising:

positioning said gap at the side of a wearer's neck, guiding said sleepy heads neck pillow towards the wearer's neck; and optionally rotating said sleepy heads neck pillow such that said neck bone support is positioned at the back of the wearer's neck. If the pillow is not rotated, it can be still be worn as a "side use" as described in greater detail below.

(5) The aforementioned method of donning a sleepy heads neck pillow on a wearer, wherein the pillow further comprises an upper back bone support that is extended down at an angle from the bottom edge of the neck bone support so that the upper back bone support is configured to give extra support to the neck and upper back of the user, and wherein the optional step of rotating the sleepy heads neck pillow causes the upper back bone support to be positioned on one of the wearer's shoulders.

(6) A method for using the sleepy heads neck pillow according to any one of (1) to (3), in a manner that the wearer does not wear the pillow on their neck but lays their face down on the pillow.

(7) A method for using the sleepy heads neck pillow according to any one of (1) to (3), in a manner that the sleepy heads neck pillow is used as a lower back use to give support to the lower back, hips, butt and spine.

DETAILED EXPLANATION OF THE INVENTION

The sleepy heads neck pillow of the invention will help people sleep while sitting up. The reason that the sleepy heads neck pillow of the invention is unique is because there is a bone structure support inside the pillow that is connected to the clip/strap system.

The pillow ("Sleepy Heads Neck Pillow") shape is unique because of the shape of the bone structure that is fully incased in the pillow.

In accordance with certain embodiments, the bone structure support comprises two parts; a neck bone support and an arm bone support, which is made to give maximum support and great comfort to the head and neck. In accordance with certain embodiments, the bone structure support comprises three parts; a neck bone support, an arm bone support and an upper back bone support, which is made to give maximum support and great comfort to the head, neck and upper back.

In accordance with certain embodiments, since there is a clip/strap system that is secured to the seat, optimum support is given to the head, neck, and upper back.

Sleepy Heads Neck Pillow of the present invention is also unique because there can be a shoulder padding support built into the pillow.

In accordance with certain embodiments, the Sleepy Heads Neck Pillow of the present invention consists of five different main parts; a pillow, a bone structure, an adjustable clip/strap system, shoulder support padding, a pillow cover and a clip system cover.

Sleepy Heads Neck Pillow of the present invention is explained in more detail by referring to the attached figures.

Figure 1:
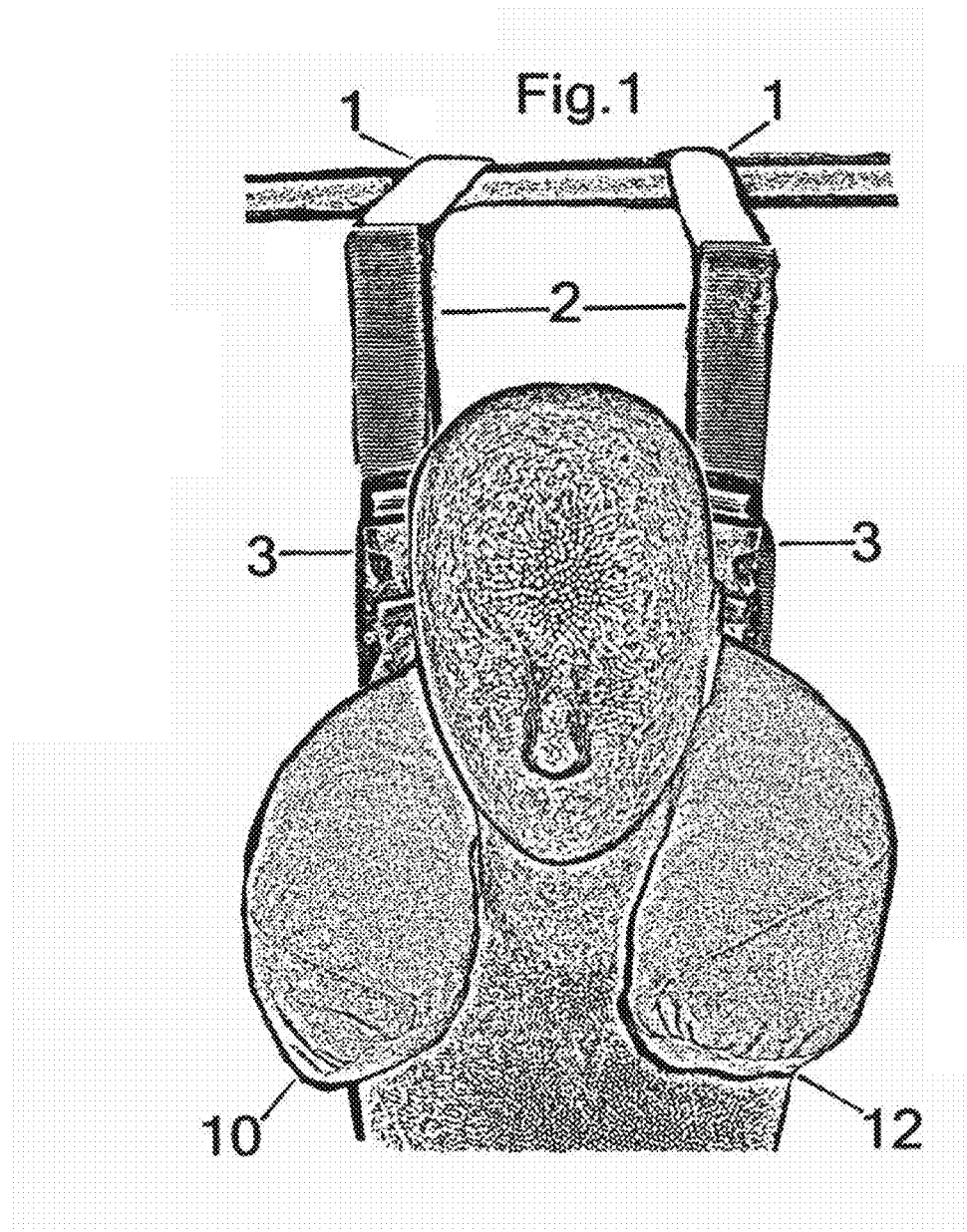
FIG. 1 illustrates a sleepy heads neck pillow with cover, strap system, and bone support belt.

FIG. 1 illustrates a sleepy heads neck pillow with cover, strap system, and bone support belt.

Figure 2:
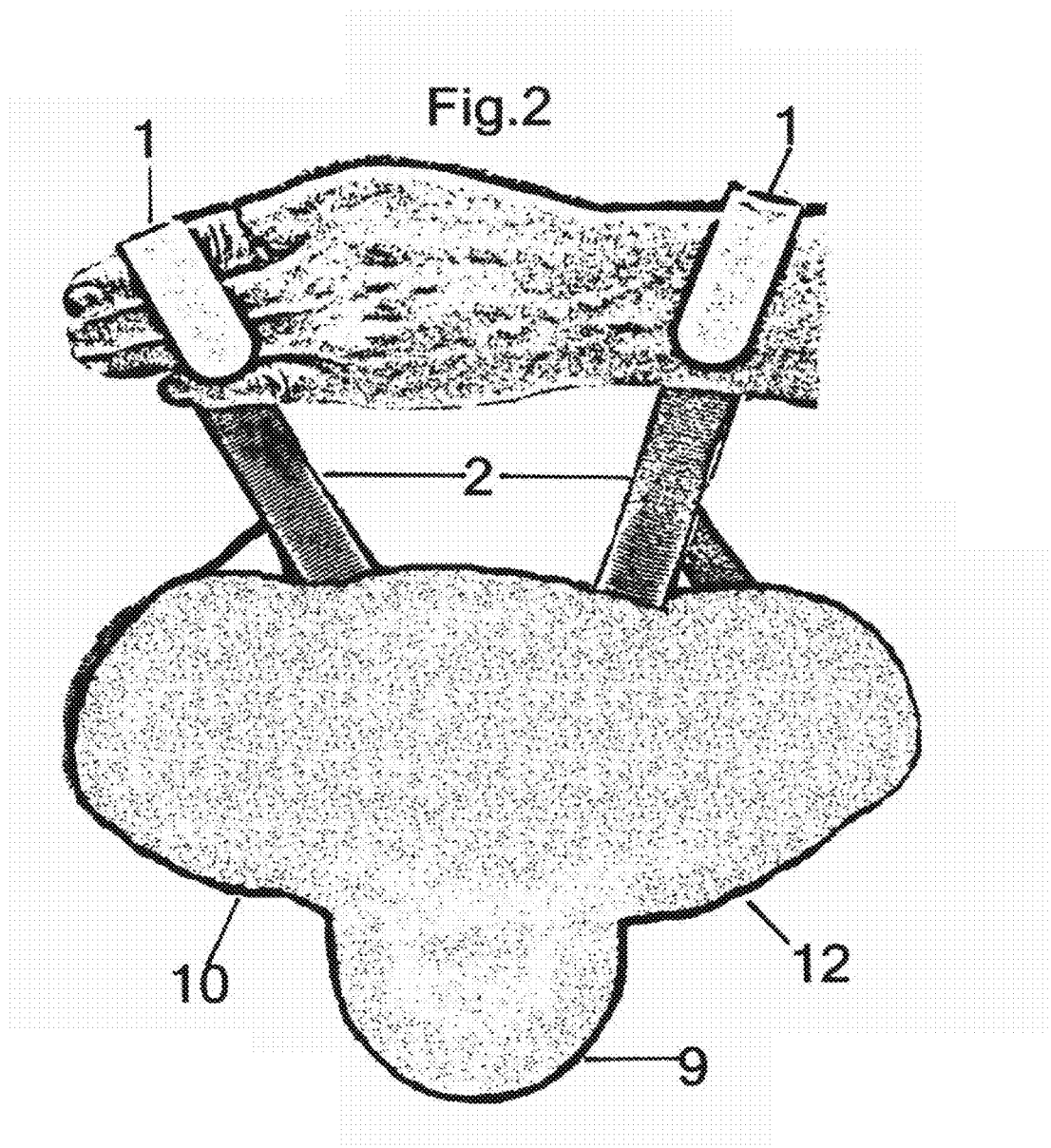
FIG. 2 illustrates a sleepy heads neck pillow with cover, back view with strap system, and bone.

FIG. 2 illustrates a sleepy heads neck pillow with cover, back view with strap system, and bone structure.

Figure 3:
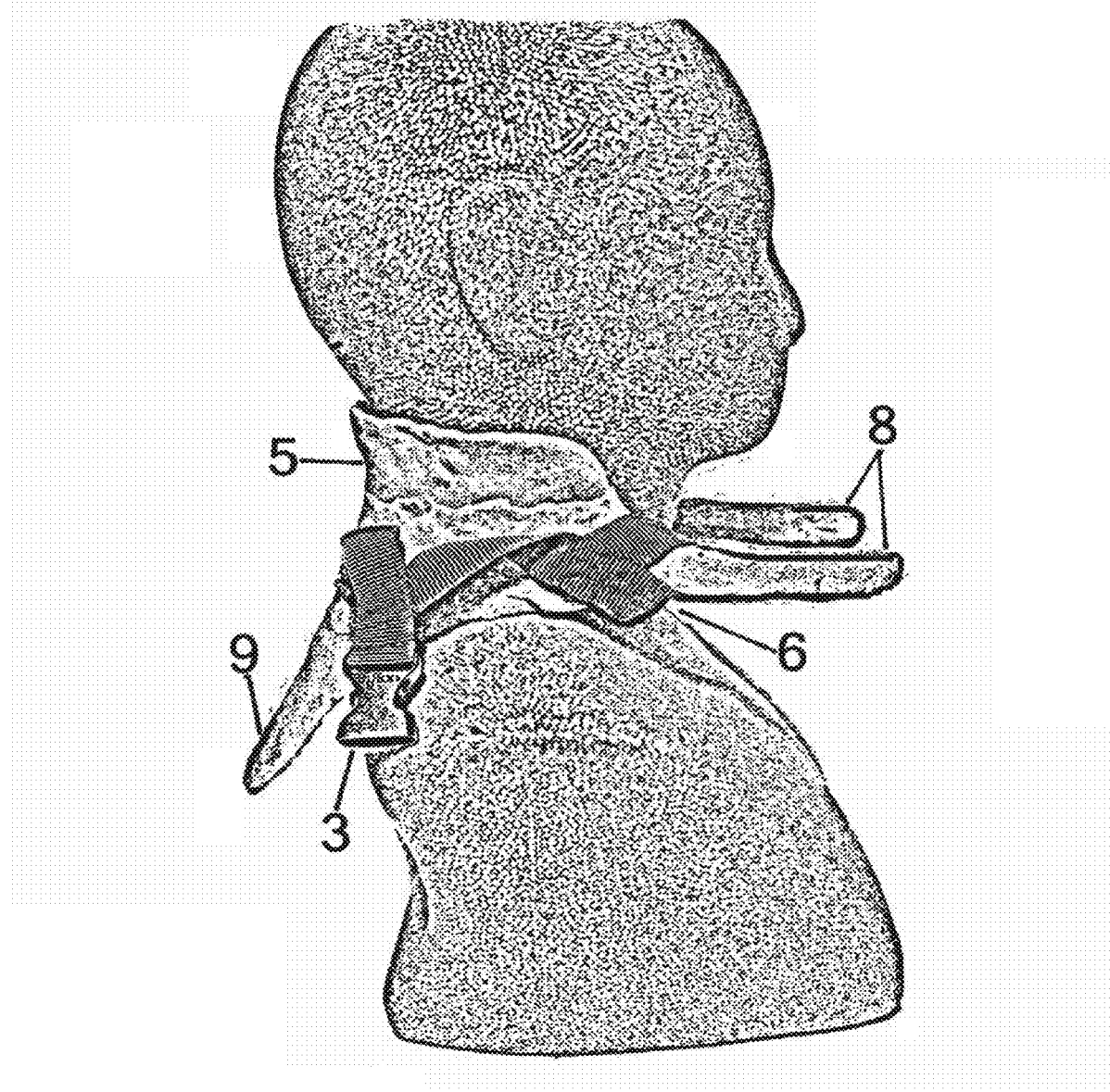
FIG. 3 shows a side view of bone structure.

FIG. 3 illustrates a side view of bone structure. The neck bone support part (5) will provide support and comfort to the neck. The arm bone (8) will support the weight of the head.

Figure 4:
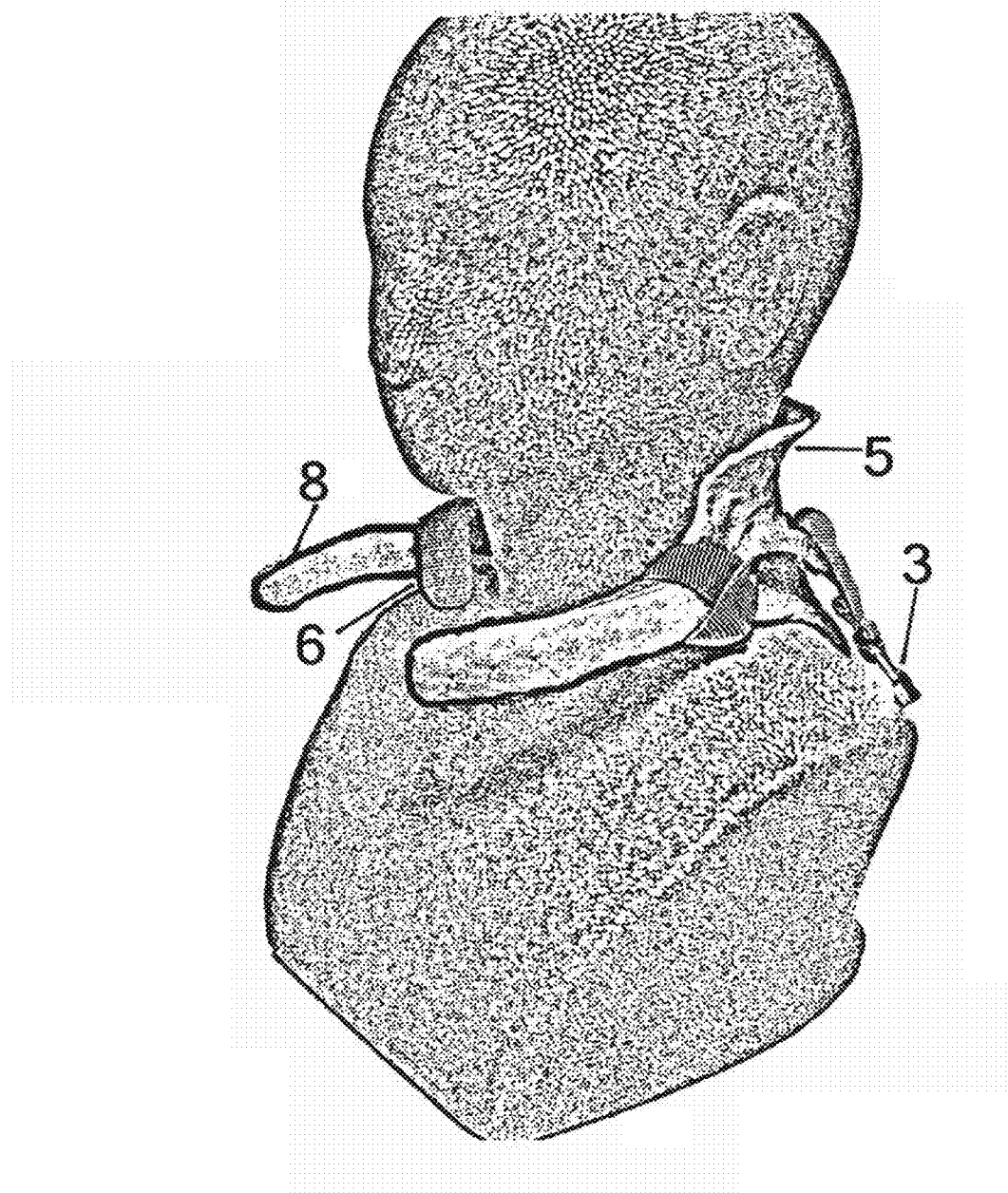
FIG. 4 shows ¾ side view of bone structure.

FIG. 4 illustrates ¾ side view of bone structure. Supportive arm strap (6) is on each side of the arm bone, which is connected to the bone structure.

Figure 5:
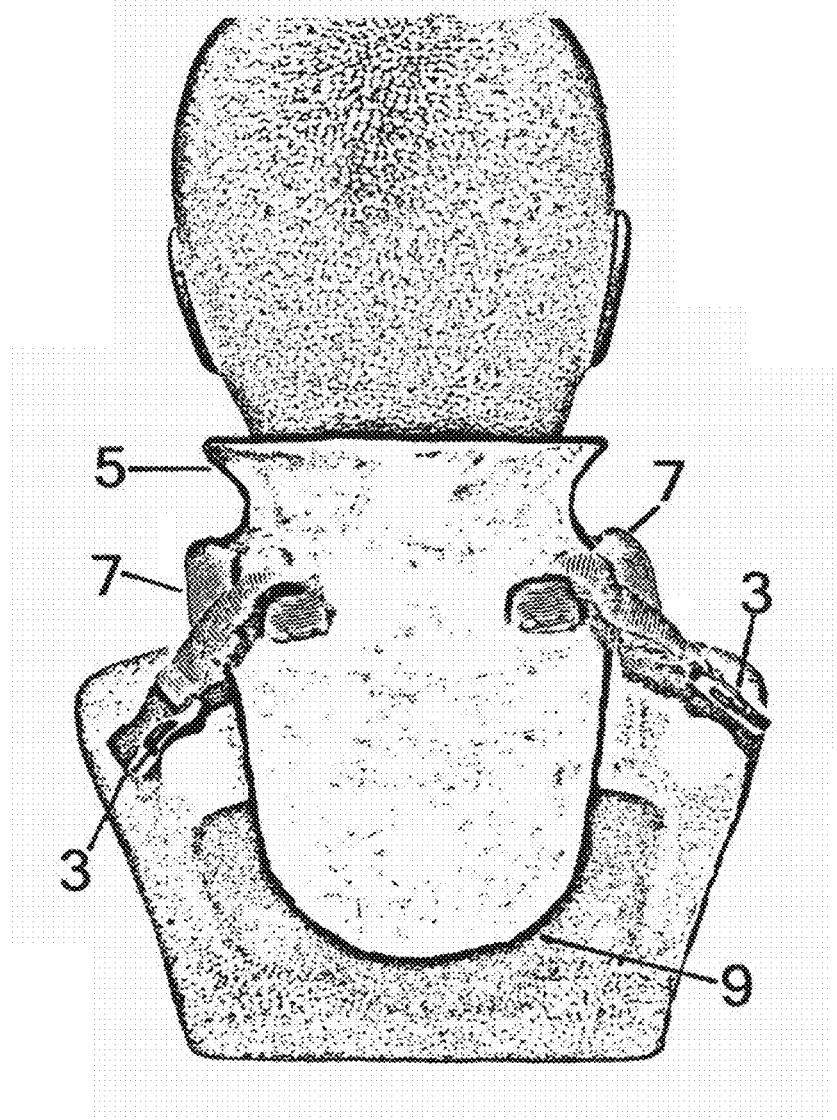
FIG. 5 shows a back view of bone structure.

FIG. 5 illustrates a back face of bone structure. The support belt (7) will be securely connected to the back of the bone structure. Element (9) indicates an upper back bone support. The back bone part will support the upper back.

Figure 6:
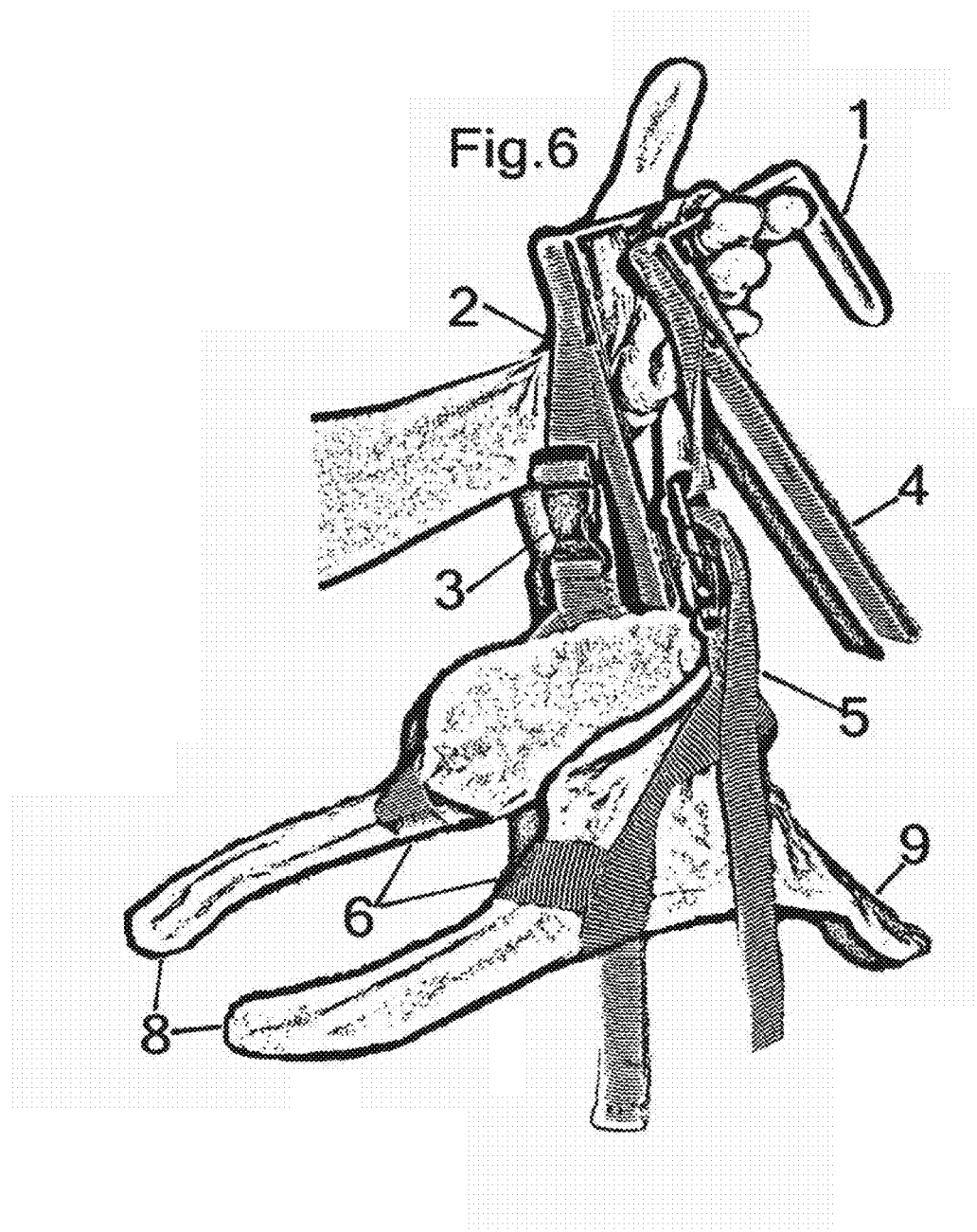
FIG. 6 illustrates a full strap system with bone structure outside pillow.

FIG. 6 illustrates a full strap system with a bone structure outside of the pillow.

Figure 7:
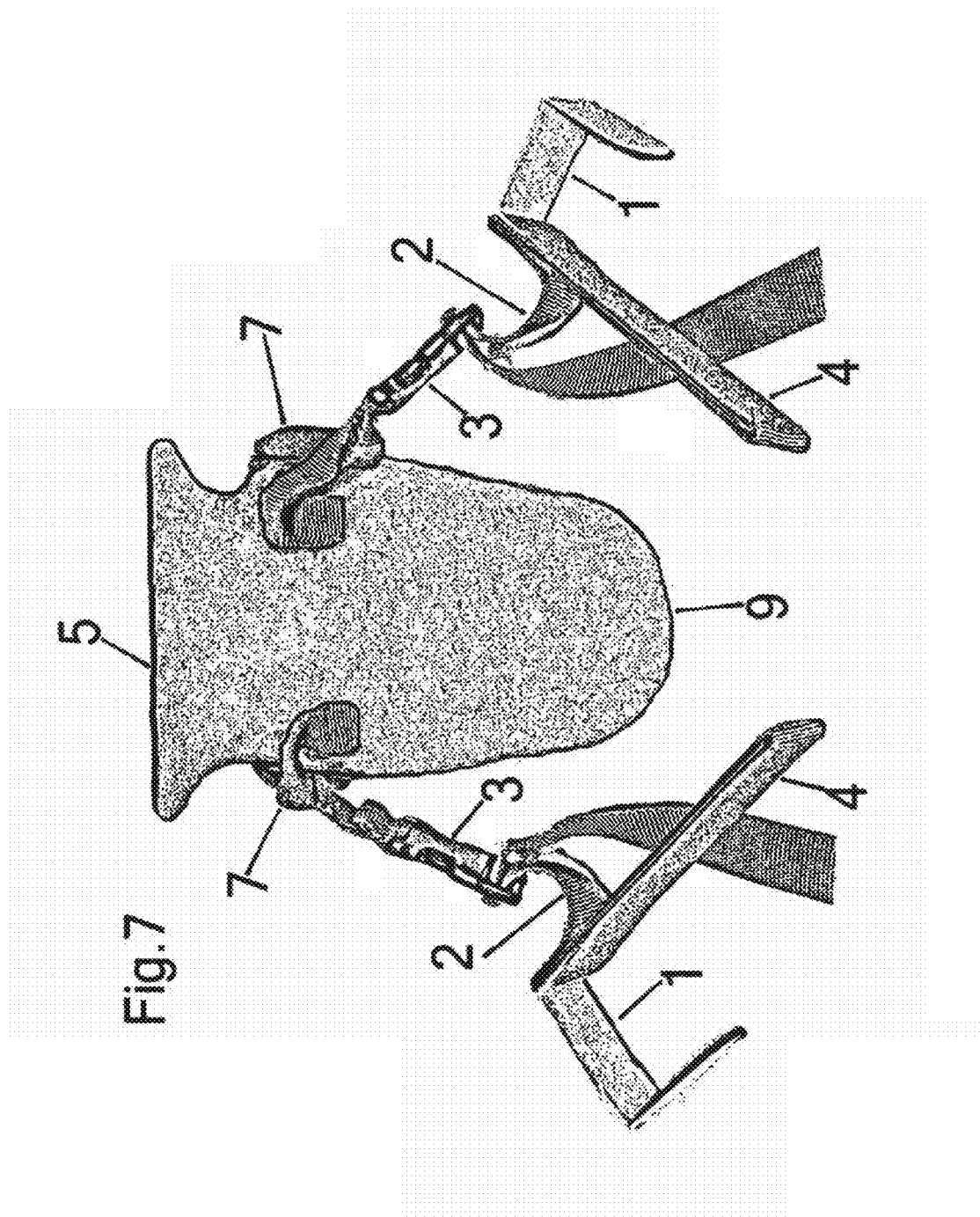
FIG. 7 illustrates a full strap system.

FIG. 7 illustrates a full strap system. The seat clips are adjustable for the thickness of the seats (car seats, airplane seats, etc.) Supportive seat brace also gives support on the seat. The seat strap length can be adjusted. The straps that are connected to the bone structure are detachable from the seat straps.

Figure 8:
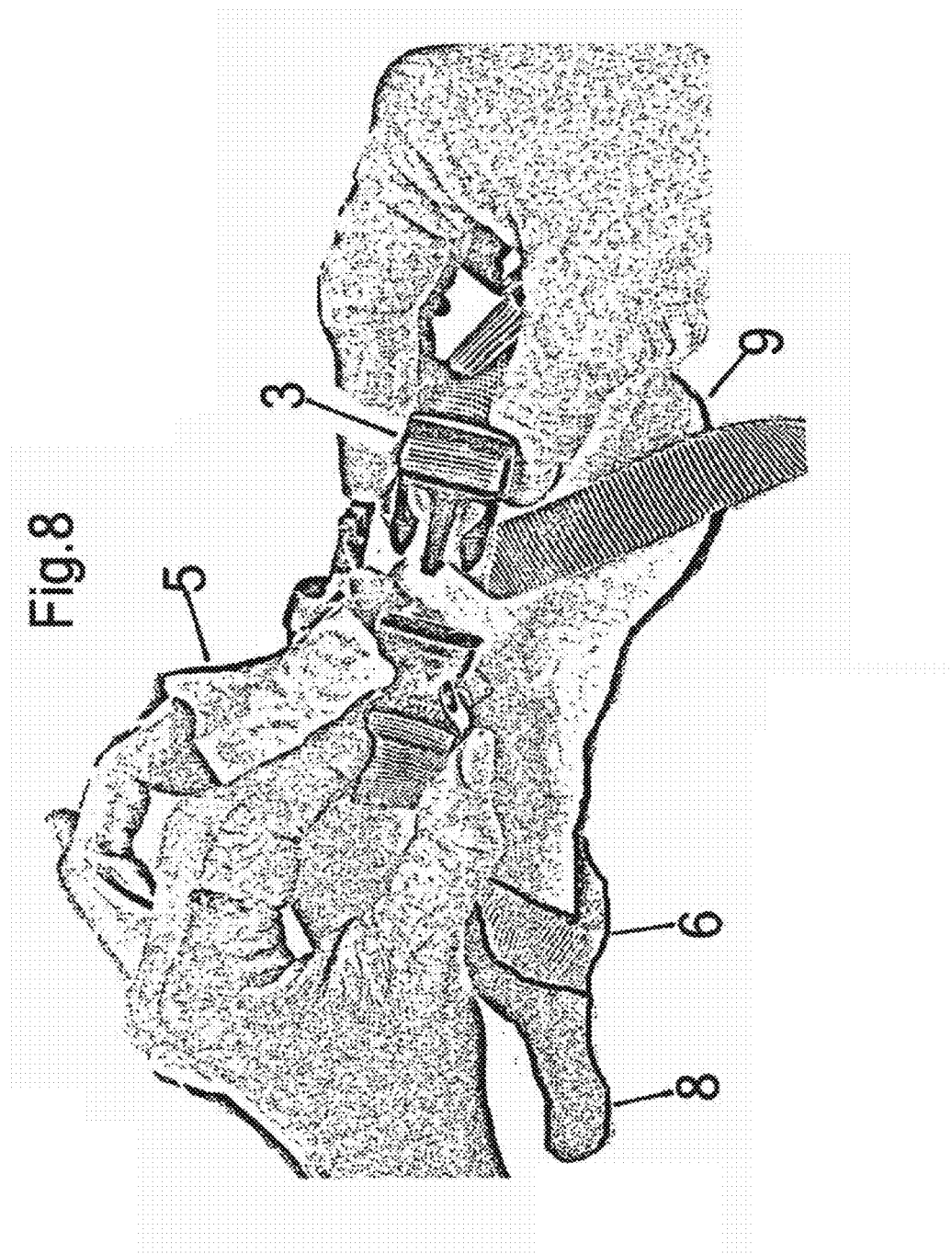
FIG. 8 illustrates a detachable clip system.

FIG. 8 illustrates a detachable clip system; clip on bone structure strap, clip on seat strap.

Figure 9:
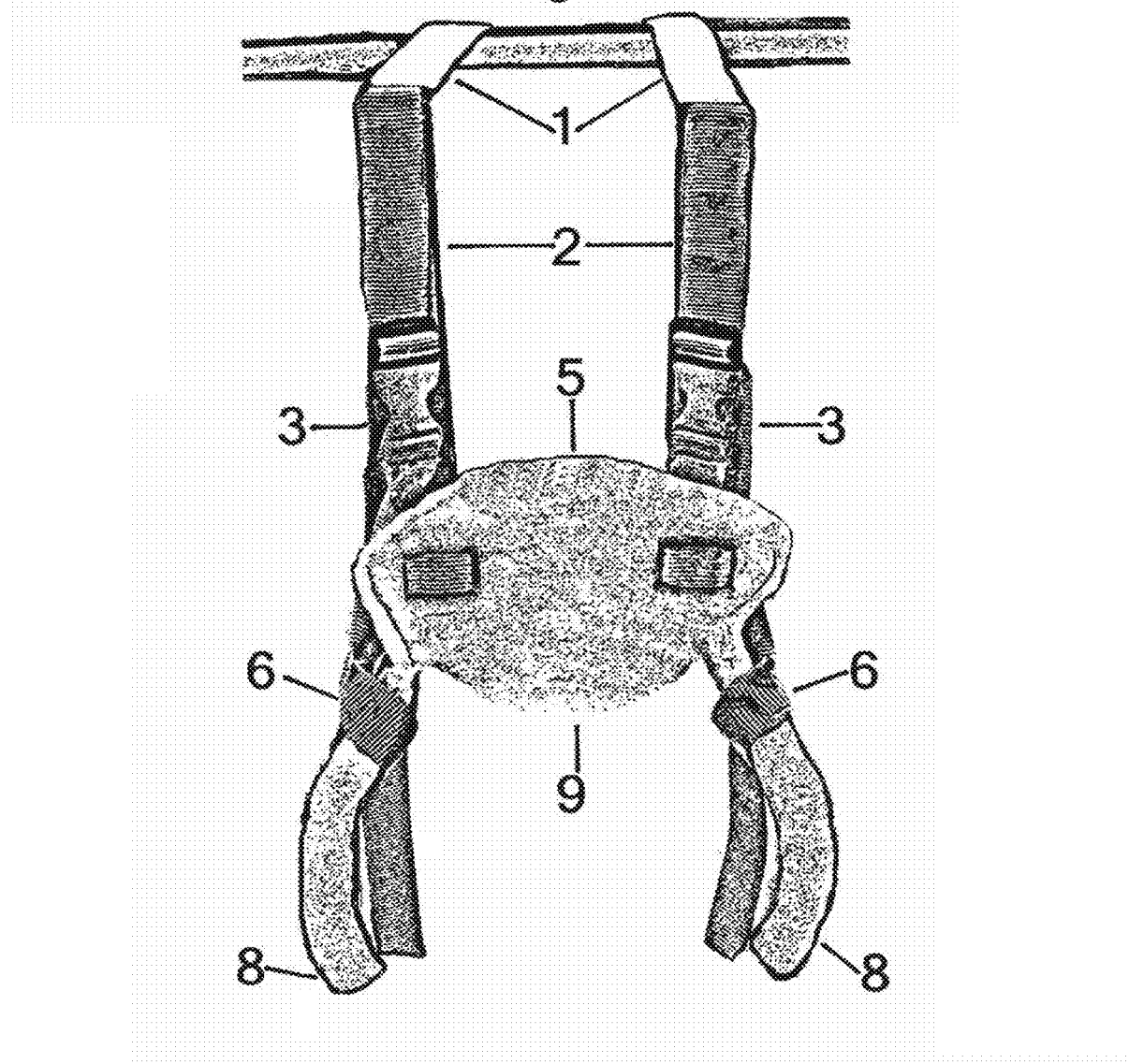
FIG. 9 shows a hanging strap view.

FIG. 9 shows a hanging strap view; indicating adjustable seat clips (1), adjustable seat straps (2), detachable clips (3), neck support bone (5), upper back bone support (9), supportive arm straps (6), and arm bone (8).

Figure 10:
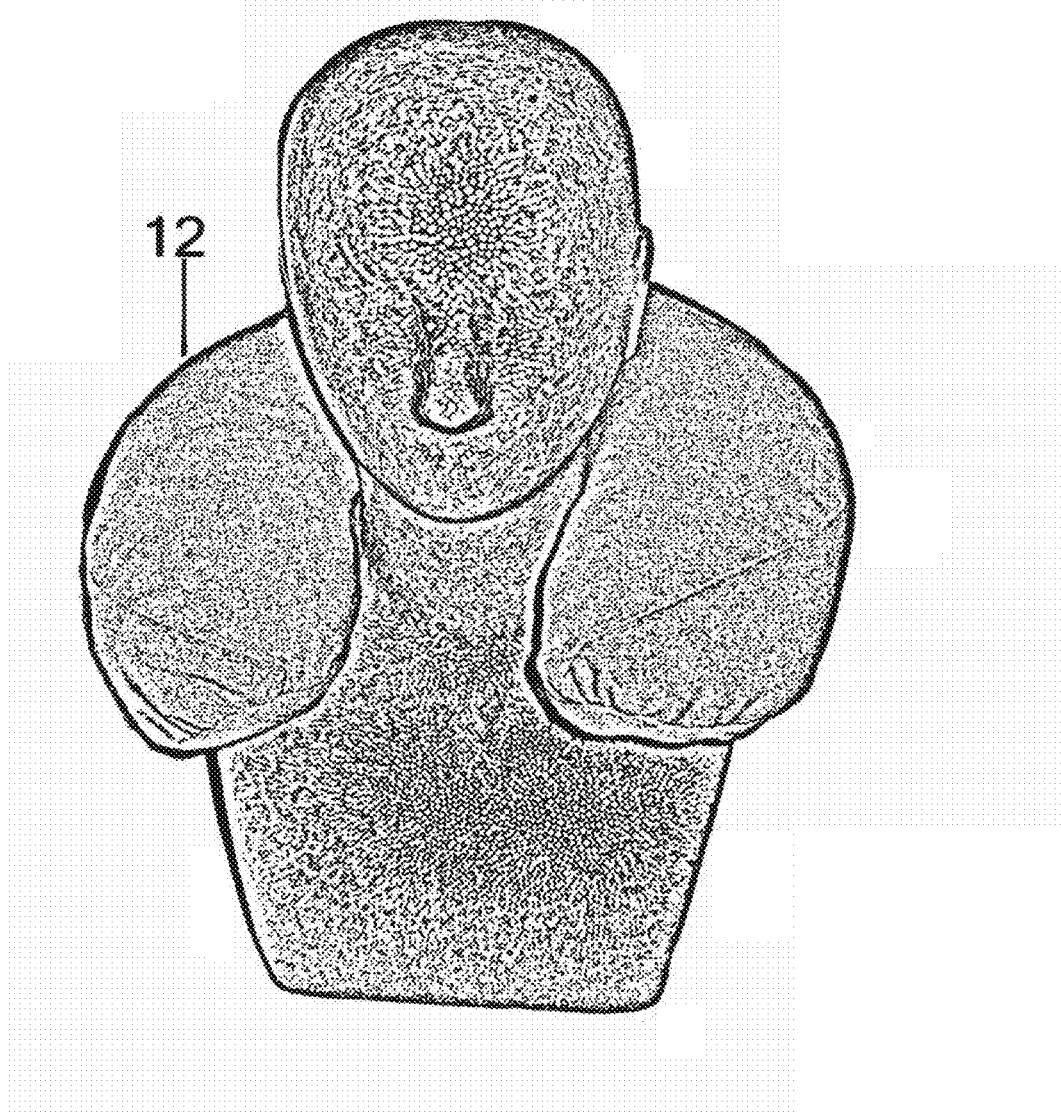
FIG. 10 shows a front view of the pillow with a pillow cover (12).

FIG. 10 illustrates a front view of the pillow with a pillow cover (12).

Figure 11:
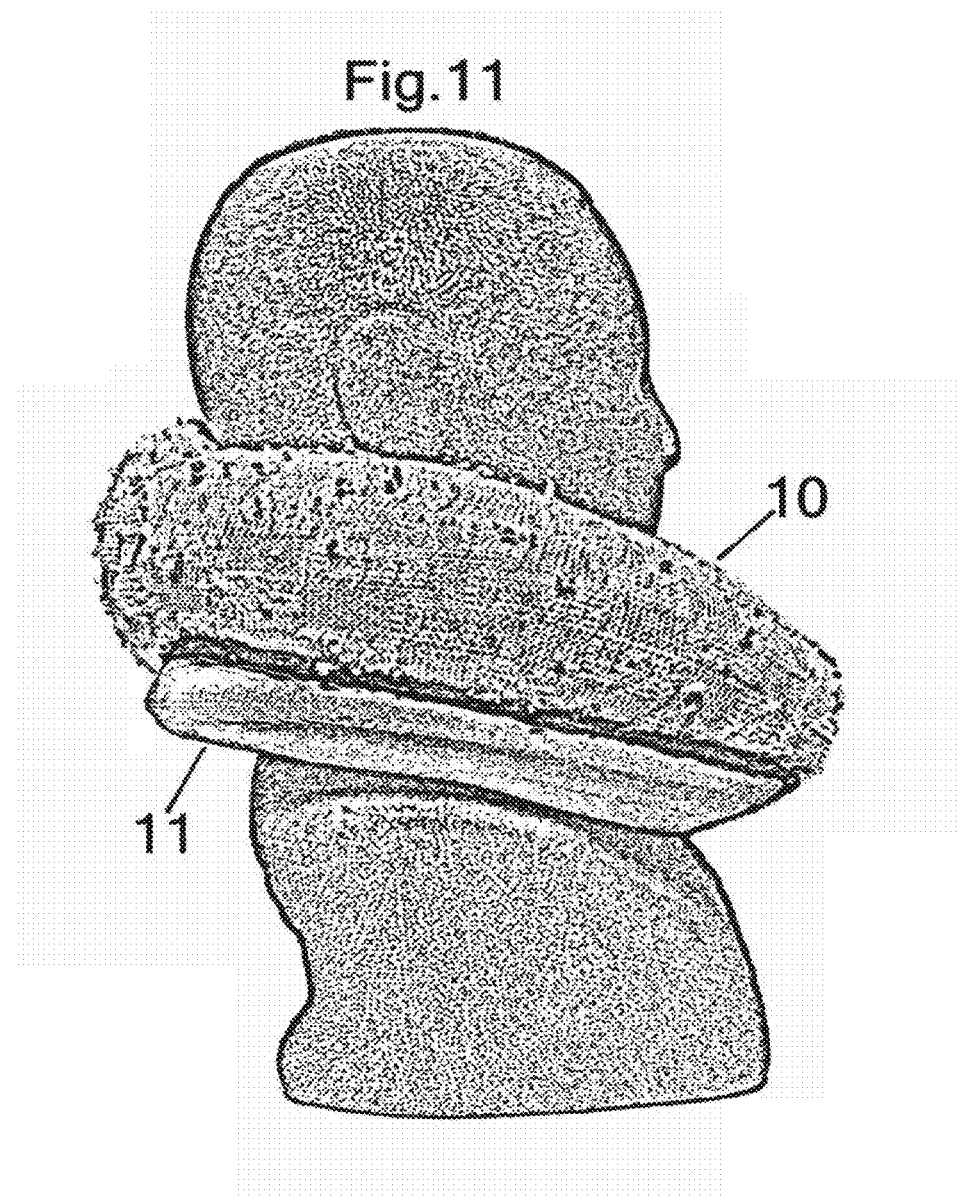
FIG. 11 shows side view of pillow, shoulder part, indicating pillow without bone and without cover (10), and shoulder support padding (11).

FIG. 11 shows a side view of the pillow and shoulder part, showing a pillow (10) with shoulder support padding (11) and without the bone structure and without a cover.

Figure 12:
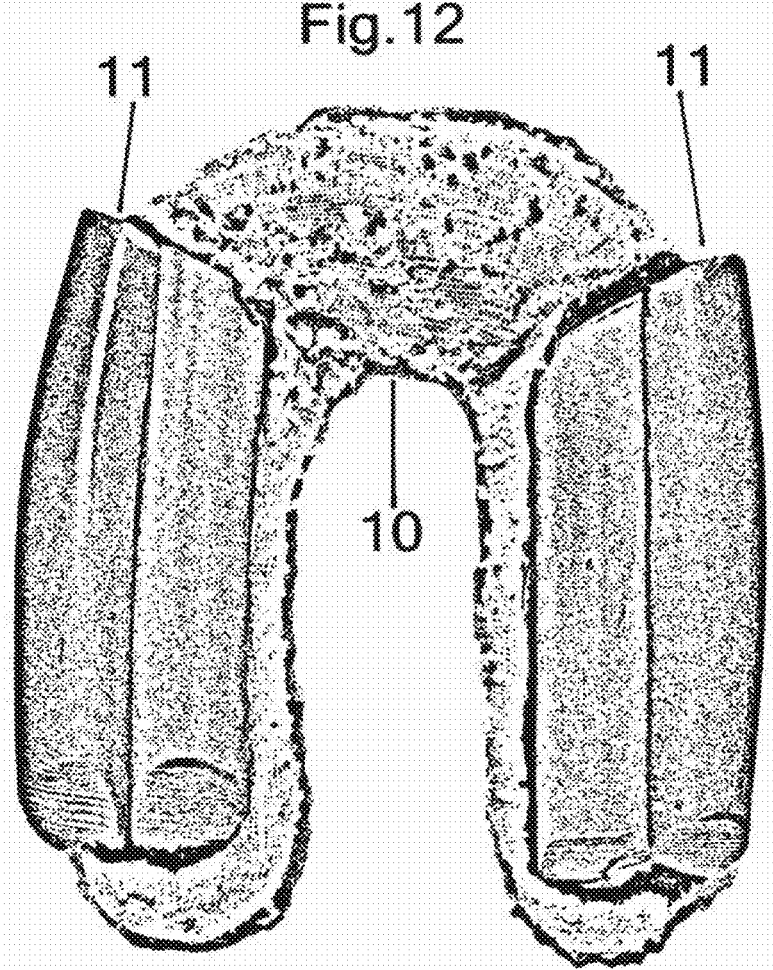
FIG. 12 shows a bottom pillow view.

FIG. 12 shows a bottom pillow view, showing the pillow (10) without the bone structure, with cover (10), and shoulder support padding (11).

Figure 13:
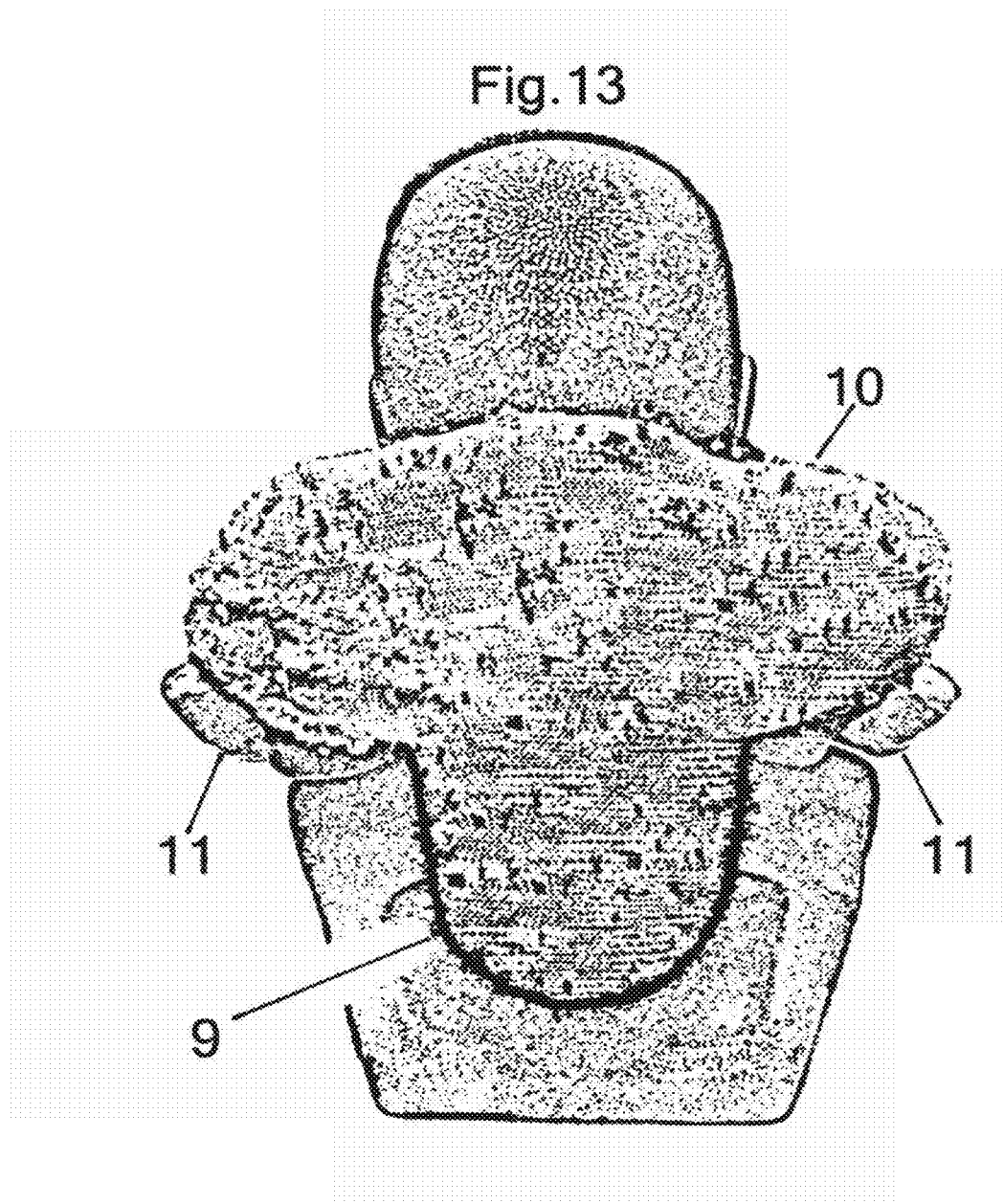
FIG. 13 shows a back view of pillow (without cover, and straps).

FIG. 13 illustrates a back view of pillow (without cover, and straps), indicating pillow (10), shoulder padding (11), and upper back bone support (9) inside the pillow (10).

Figure 14:
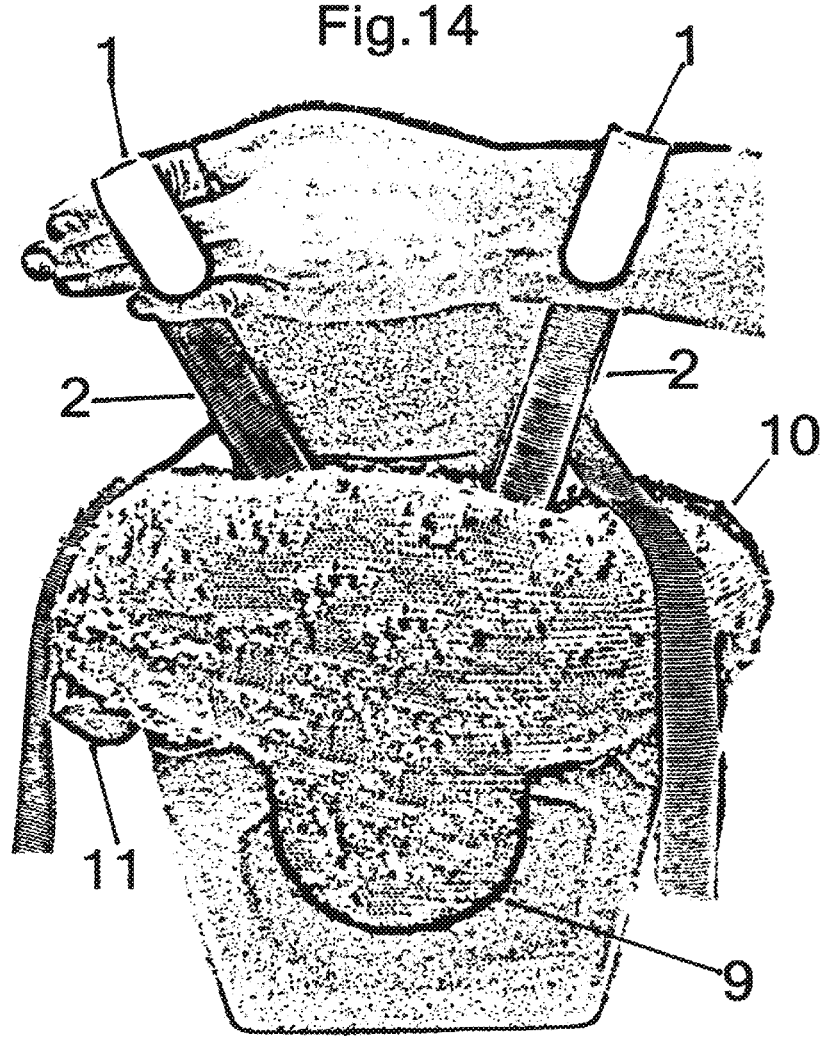
FIG. 14 illustrates a complete pillow and straps (back view without cover).

FIG. 14 illustrates a complete pillow and straps (back view without cover); indicating adjustable seat clips (1), adjustable seat straps (2), pillow (10), shoulder support padding (11), and upper back bone support in pillow (9).

Then, the parts indicated in the attached figures are explained in detail as below.

Adjustable Seat Clips (1):

In accordance with certain embodiments, the adjustable seat clips (1) are made of strong durable hard plastic. The clips can be made of two pieces. One is the back clips which sets on the back of the seat is enclosed in a strap which is connected to the adjustable seat straps (2). Another is the front part of the clips which sets on the front part of the seat, and continues as supportive seat brace (4). The front clips slides into the back clips which makes it adjustable on the seat. The head weight on the pillow; because it is connected to the adjustable seat straps (2), will cause the back seat clips to come forward, and make the clips secure on the seat.

Adjustable Seat Straps (2):

In accordance with certain embodiments, the adjustable seat straps (2) can be made of strong durable material. They are connected to the seat clips (1). They can be made to be adjustable for any length, or height of the person using the pillow.

Detachable Clips (3):

The detachable clips (3) can be made of a strong durable hard plastic. It is used to make the Sleepy Heads Neck Pillow detachable from the adjustable clip/strap system.

Supportive Seat Brace (4):

The supportive seat brace (4) can be made of strong durable hard plastic; it gives extra support on the front of the seat and keeps the clips closed by the weight of the head on the pillow.

Neck Bone Support (5):

In accordance with certain embodiments, the Neck Bone Support (5) can be made of a strong durable hard plastic which the whole bone structure that consists of the three parts; (5), (8) and (9) which may be adjustable, is made of. It is the neck support of the bone structure of the pillow. It conforms, fits the shape of the neck which gives high support, and comfort to the neck of the pillow. The bone of the pillow can be one piece that consists of three parts; part (5), part (8) and part (9).

In accordance with certain embodiments, the neck bone support has a top edge 70, a bottom edge 71, a left edge 73 and a right edge 74. The bone support has an intermediate region 72 connecting the top and bottom edges. The neck bone support, from the top edge 70 to the bottom edge 71 can be any length, width or thickness. The neck bone support can be any shape that is configured to conform to and support the back of the neck of the user.

Supportive Arm Strap (6):

In accordance with certain embodiments, the supportive arm strap (6) can be made of strong durable material, which is the same material as all of the straps on the pillow. It wraps around each side of the arm bone (8), so that it gives extra support and balance keeping the pillow in a horizontal position. The supportive arm strap (6) is connected to the support belt (7).

Support Belt (7):

In accordance with certain embodiments, the Support Belt (7) can be made of a strong durable material, which is the same material as all of the straps in the pillow. It is securely fixed through a hole in the back bone structure. The support belt (7) is connected to the supportive arm strap (6) which continues up to the detachable clips (3).

Arm Bone Support (8):

In accordance with certain embodiments, the arm bone support (8) can be part of the bone structure that is extended over the shoulder from the neck bone support (5). The bone structure support can have one or more arm bone supports. When the bone structure support has two arm bone supports, the length of each of the two arm bone supports may be the same (i.e., a pair of the same two arm bone supports) or different. The one or two arm bone supports respectively extend from the left and/or right edges of the neck bone support. The arm bone support can be any shape, length or width. Preferably, a length of each arm bone is substantially greater than a width of each arm bone support so that the arm bone supports are configured to extend forwardly of the shoulders of the user to support the user's head when the head is resting to the side. Preferably, the arm bone support is an arm shape structure which gives support to the head when the head is resting on the side. Alternatively, the arm bone support may consist of a number of arm bone-like shape structures. Each of the arm bone-like shape structures may be aligned in parallel or arranged so that they are not in parallel. In accordance with certain embodiments, the bone structure support can have more than two arm bone supports. In accordance with certain embodiments, the length of each of the arm bone supports (arm bone-like shape structure) may be the same or different.

Figure 15:
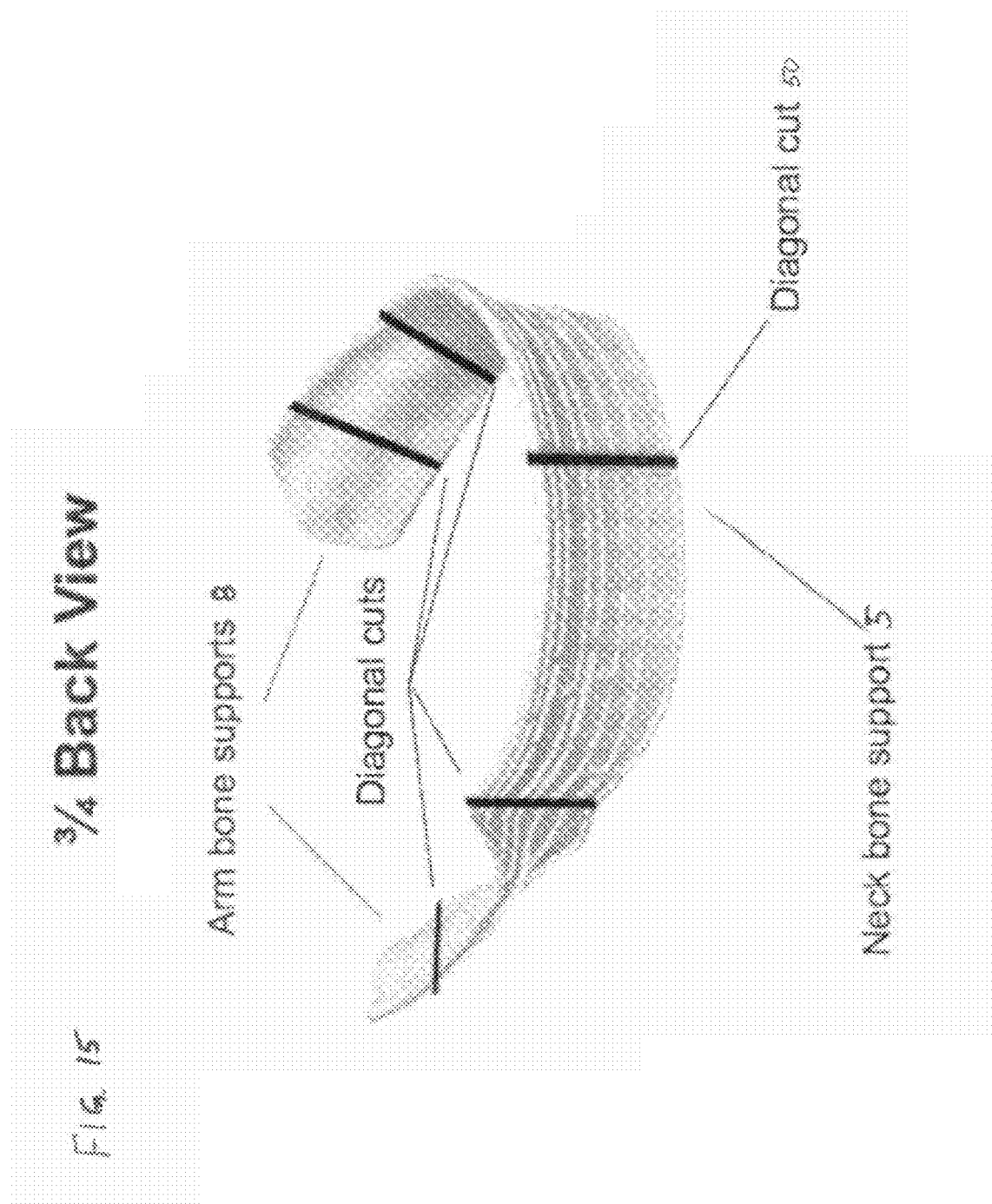
FIG. 15 is ¾ back view of a bone structure with diagonal cuts in accordance with certain embodiments.
Figure 26:
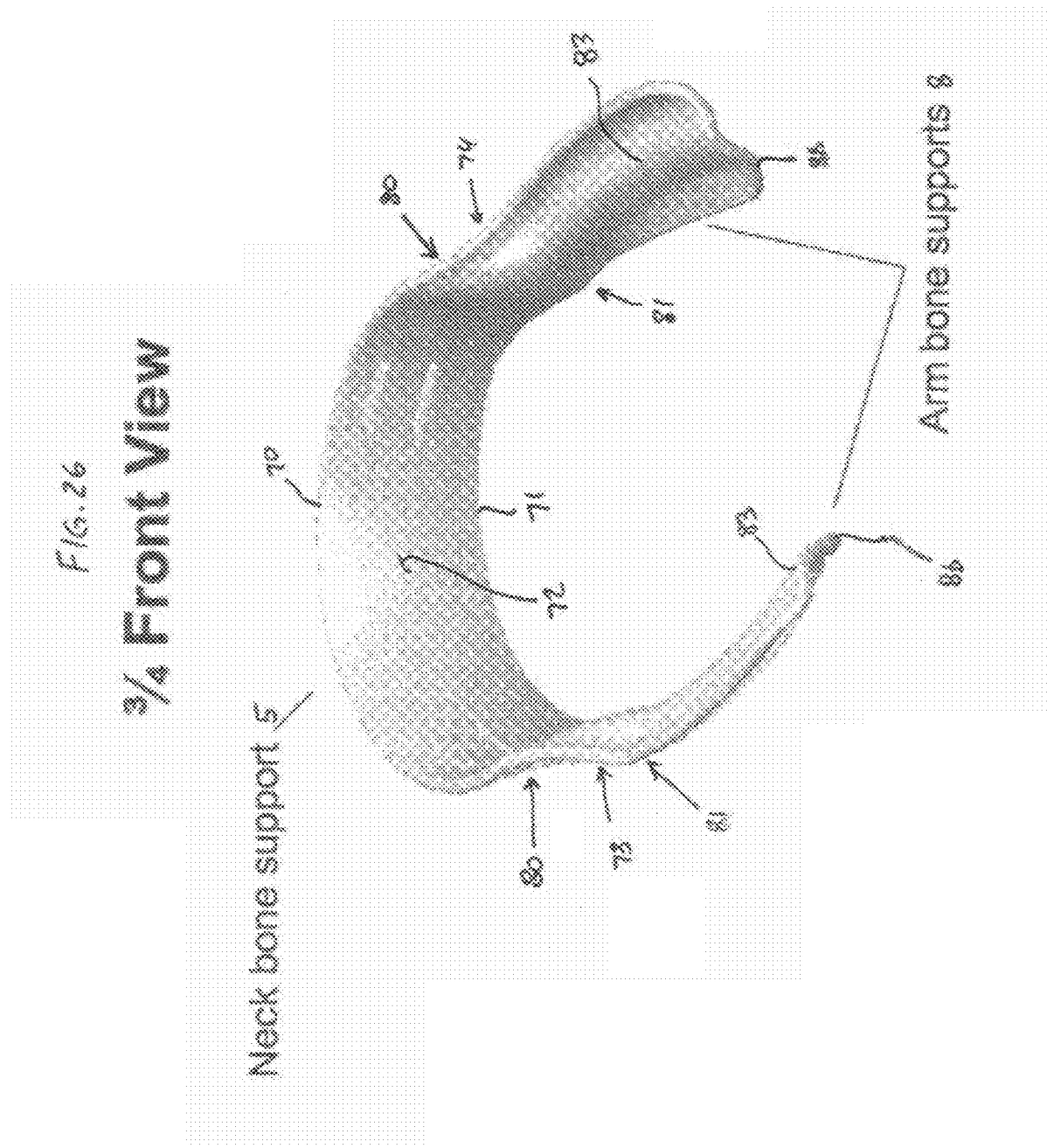
FIG. 26 is a ¾ front view of a neck bone support in accordance with certain embodiments.
Figure 27:
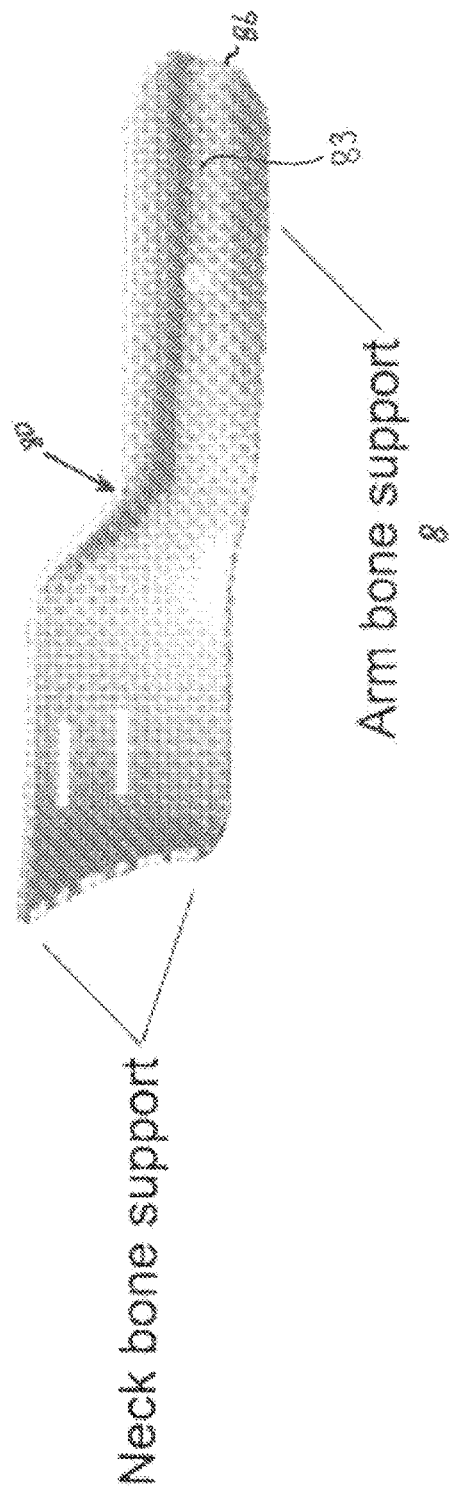
FIG. 27 is a side view of the neck bone support of FIG. 26.
Figure 28:
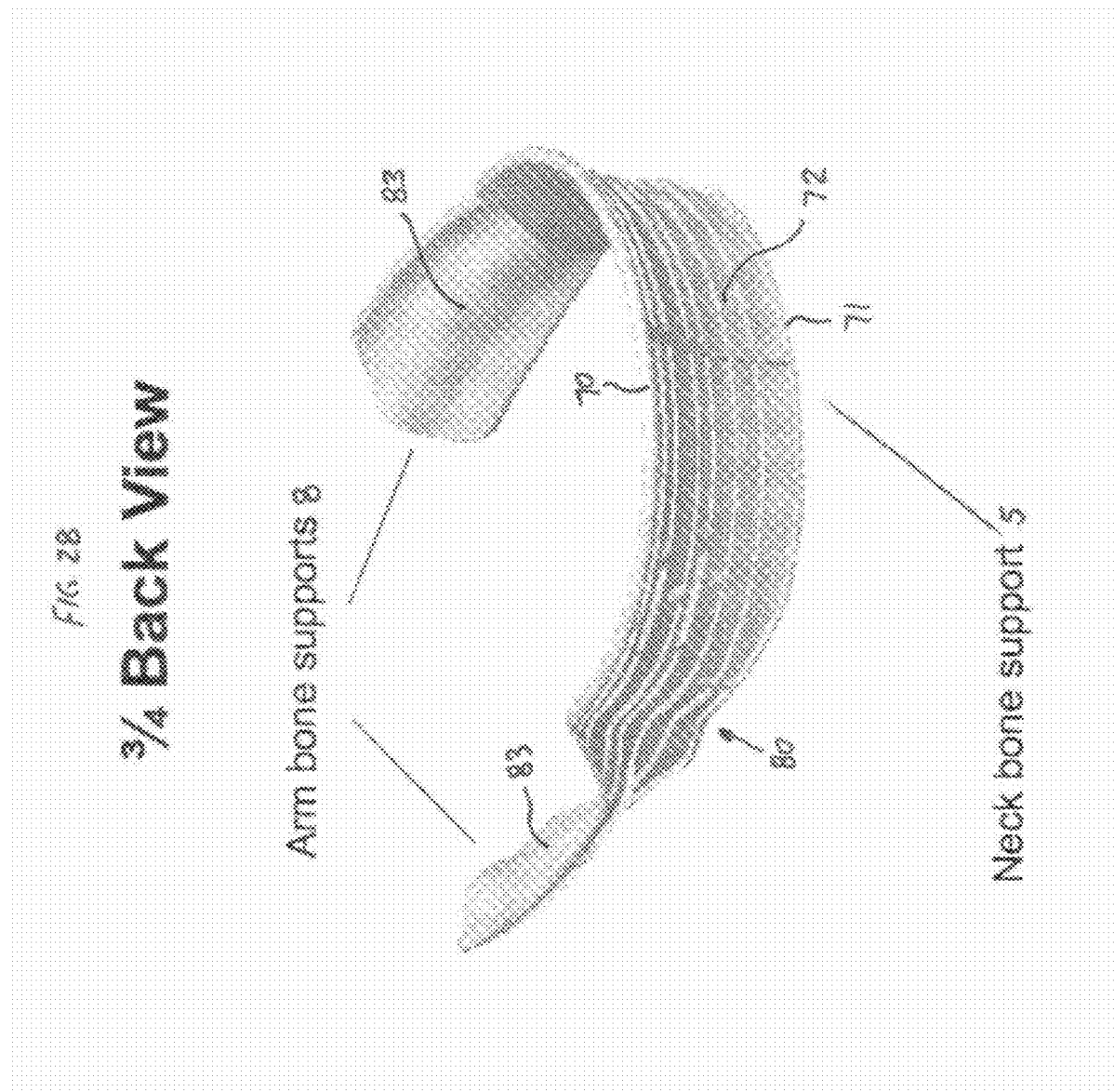
FIG. 28 is a ¾ back view of a neck bone support in accordance with certain embodiments.

FIGS. 26-28 show a neck bone support (5) in accordance with certain embodiments, where each of the arm bone supports 8 extend forwardly from the neck bone support and outwardly (i.e., away from each other) at an angle at points 80. Thus, each arm bone support 8 bends at point 80. The arm bone supports 8 continue to extend away from the back of the neck bone from that bend and then taper inwardly back towards each other at points 81, and terminate at the distal free ends 8b thereof. In accordance with certain embodiments, the arm bones 8 also can be bent so that the top edge of each arm bone is bent outwardly relative to the bottom edge of each arm bone, as best seen in FIGS. 15 and 26. Each arm bone 8 can also have a wave-like contour 83 along its length, whereby the longitudinal middle portion of each arm bone protrudes inwardly as shown in FIG. 26.

Upper Back Bone Support (9):

According to the more preferable embodiment of the invention, the bone structure support comprises an upper back bone support. The upper back bone support (9), a part of the bone structure support that is extended down the upper back; gives extra support to the neck, and upper back. The upper back bone support is extended down at an angle from the bottom edge of the neck bone support so that the upper back bone support is configured to give extra support to the neck and upper back of the user. All of the three parts of the born structure which may be adjustable (5), (8) and (9) combined together create a perfect balance, comfort to give the head, neck, and shoulders support with great stability on the pillow. The full bone structure support will be fully incased inside the pillow.

Pillow (10):

In accordance with certain embodiments, the pillow (10) can be made up of form fitting foam pieces. The Pillow is firm, but because of the form fitting foam pieces it also conforms to the shape of neck, and face line. It is very comfortable all around the pillow. The user of the sleepy heads neck pillow won't be able to feel the hardness of the bone structure that is inside of the pillow.

Shoulder Support Padding (11):

In accordance with certain embodiments, the shoulder support padding (11) can be made of a firm form fitting foam material which will be placed under the pillow on both shoulders. This support will give extra comfort and stability on the shoulders.

Pillow Cover (12):

In accordance with certain embodiments, the pillow cover (12) can be made of very soft and comfortable material that will fit the pillow perfectly. The pillow cover is removable, and washable.

In accordance with certain embodiments, the bone structure support can be made up of one part or multiple parts such as two, three, four, five or more parts. The bone structure support can be adjustable by means through the combination of the bone structure parts. The bone structure support can be adjustable on any part of it through the many movable parts that is consisted of Any part or combinations of parts of the bone structure can be adjustable by any suitable means. It is able to adjust forward, backward, inward, outward, sideways, upward, downward or any combination of them all through the use of hinges, collapsible systems, springs, screws, brackets, rollers, click systems, or any other systems that can connect the bone structure together to be adjustable.

Figure 16:
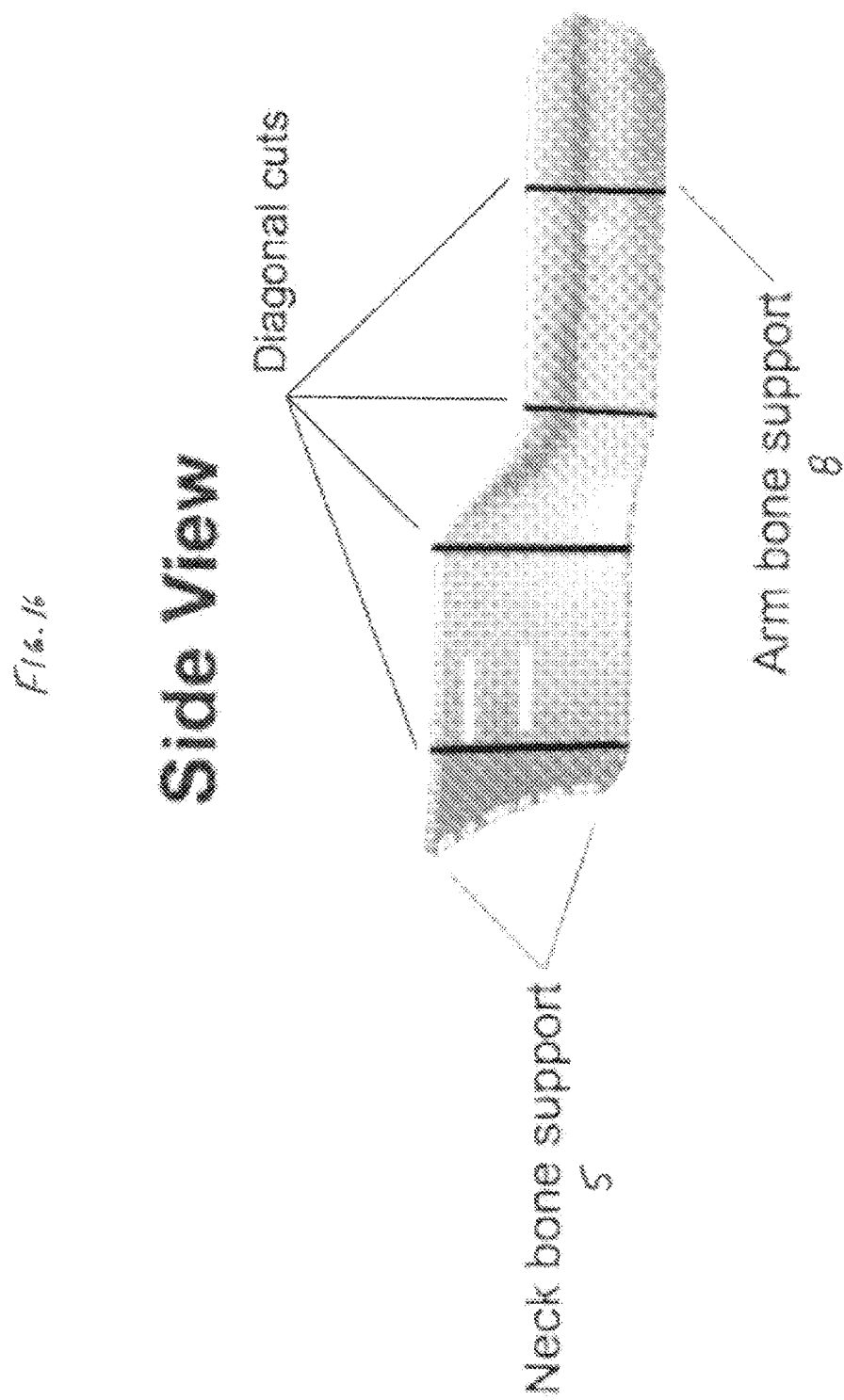
FIG. 16 is a side view of a bone structure with diagonal cuts in accordance with certain embodiments.
Figure 17:
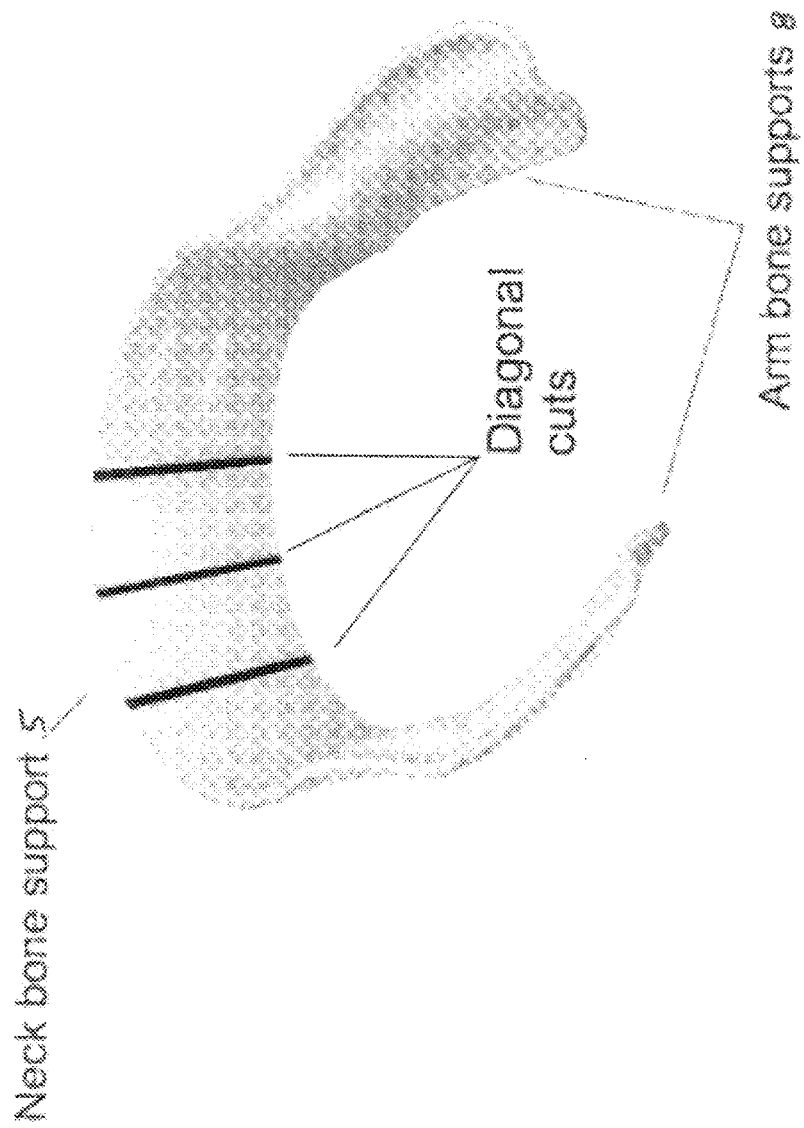
FIG. 17 is a ¾ front view of a bone structure with diagonal cuts in accordance with certain embodiments.

In accordance with certain embodiments, the one-part or one-piece bone structure support can be made up of arm bones, an upper back bone support and a neck bone support. With reference to FIGS. 15-17, diagonal cuts can be made on the bone structure where the bone structure can be collapsible or adjustable. The diagonal cuts can be made anywhere on the bone structure. The two-part or two-piece bone structure support can be split diagonally at the back of the bone structure support (diagonal cut 50 in FIG. 15) so the two parts are made up of the left and right sides of the bone structure support. The three-part or three-piece bone structure support can be split diagonally at the back of the bone structure support and the two back parts can be connected by a third part in between the two parts that makes the two back pieces move apart or move together, or just connects the two back pieces. Another three-part or three-piece bone structure support includes the case wherein the arm bones are split diagonally anywhere on each of the arm bones, so the three parts are made of arm bone parts and one back part. The four-part or four-piece bone structure support can be made up of diagonal cuts anywhere on each of the arm bones and a diagonal cut at the back of the bone structure support so the four parts are arm bone parts and two back bone parts. The five-part or five-piece bone structure support can be made up of diagonal cuts anywhere on each of the arm bones and a diagonal cut at the back of the bone structure support. The five parts are made up of arm bone parts, two back parts and one part in between the two back parts. The one part that connects the two back parts together is there so they can move apart or move together.

Figure 18:
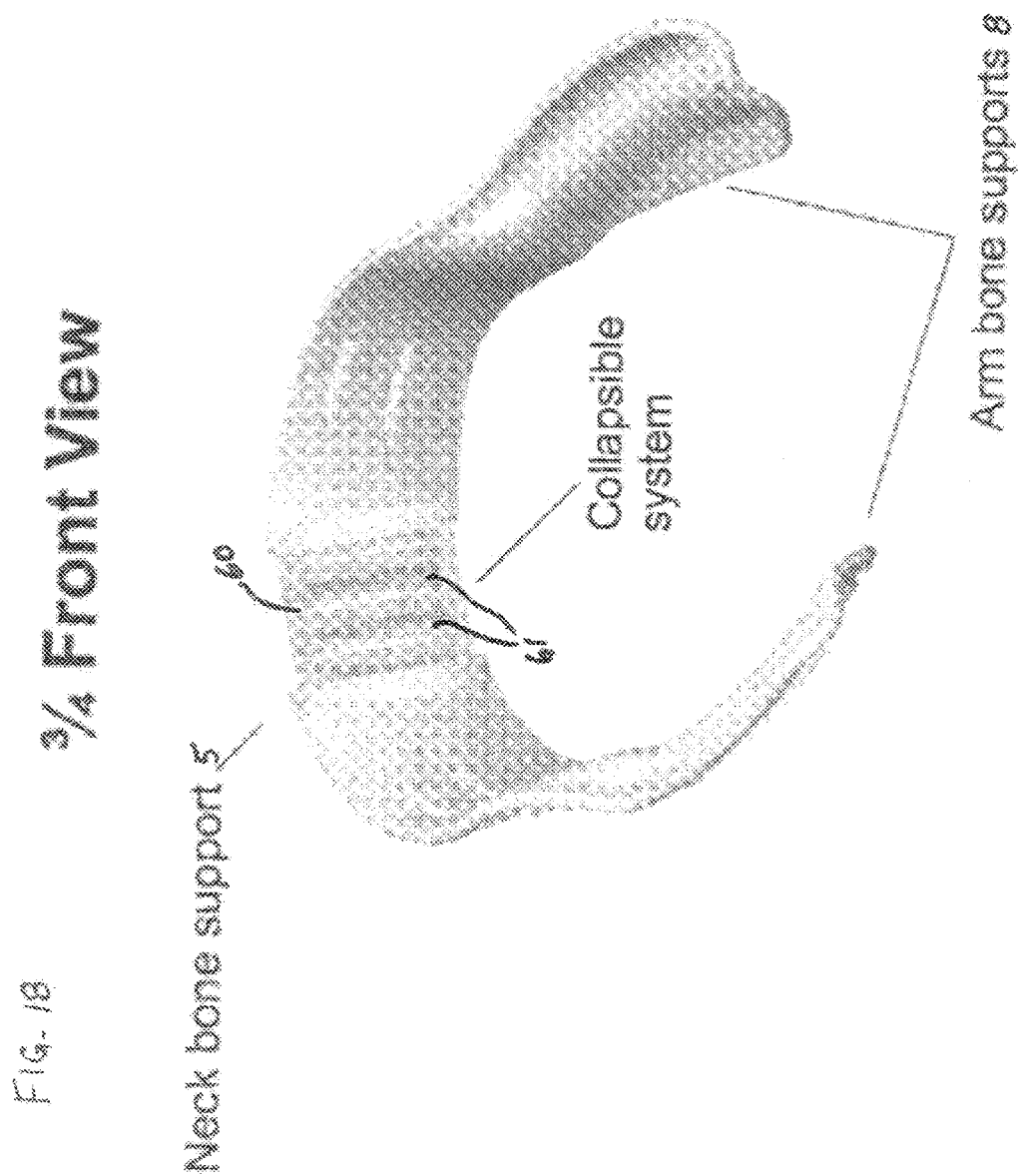
FIG. 18 is a ¾ front view of a bone structure with a collapsible system in accordance with certain embodiments.
Figure 19:
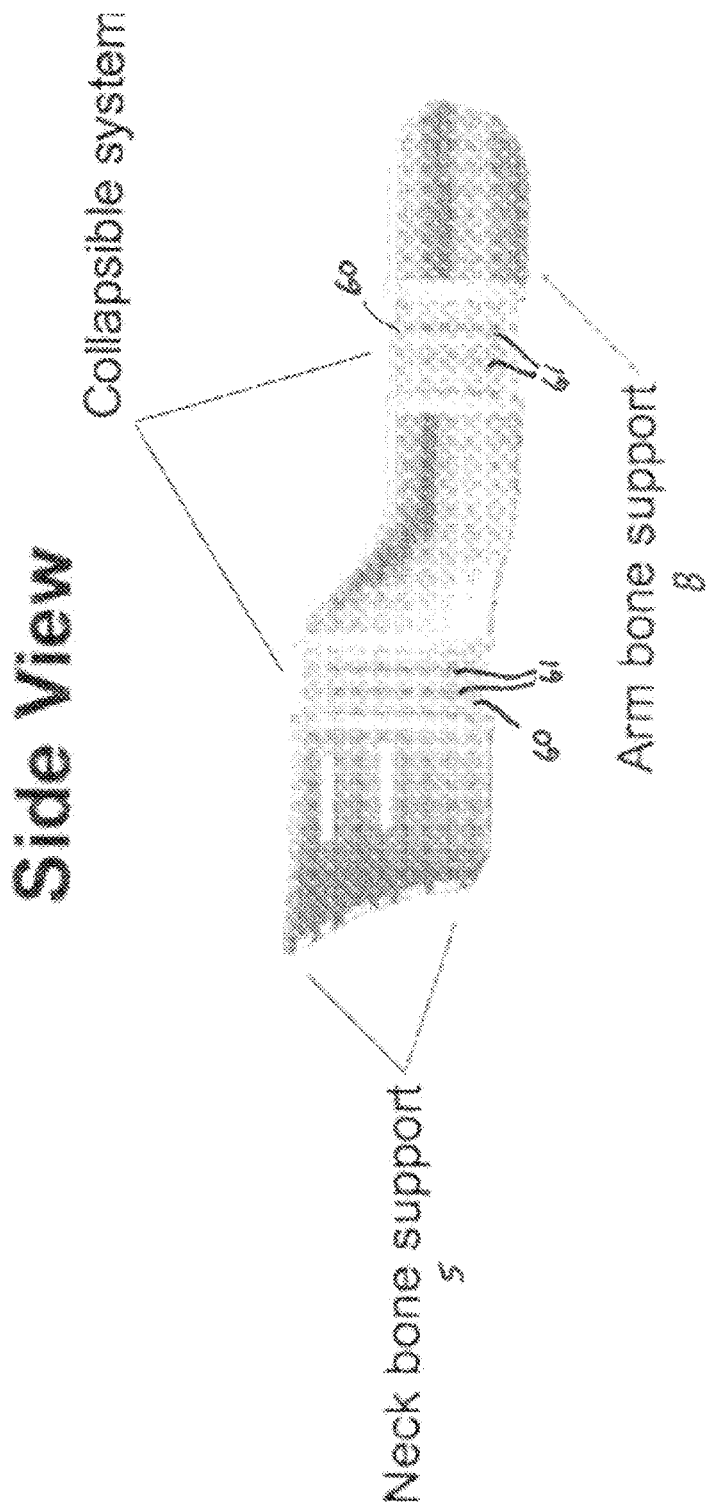
FIG. 19 is a side view of a bone structure with a collapsible system in accordance with certain embodiments.

In accordance with certain embodiments, the bone structure support can be collapsible or can be able to fold compactly or go down or inward or outward. It can be made up of a combination of compartments with one or more joints that are connected together making one bone structure support that is adjustable. The bone structure can be collapsible, it can be able to be folded compactly, inward or outward because of the joints or panels within the bone structure. The connecting joints or panels make the bone structure parts capable of sliding into or out of each other. It can be made up of a combination of compartments with one or more joints or panels that are connected together making one bone structure that is adjustable. The joints or panels within the bone structure make the bone structure parts capable of sliding into or out of each other. FIG. 18 shows a collapsible system wherein the bone structure support includes an intermediate panel 60 over which the left and right sides of the back bone can slide towards one another. The intermediate panel 60 includes one or more indentations 61 which mate with corresponding protrusions (not shown) inside the bone structure and lock the bone structure in place on the panel 60. The wearer simply chooses which indentation 61 is to be used to lock the bone structure, based on the size of the bone structure desired. As shown in FIG. 19, a plurality of such collapsible systems can be used, such as to further adjust the neck bone support and/or to adjust the length of the arm bone support.

Any part or combination of parts of the bone structure support can be adjustable by any given way. It is able to adjust forward or backward or inward or outward or sideways or upward or downward or any combination of them all.

The bone structure support can be made of a hard, semi-hard, soft, firm, pliable, flexible or bendable material or a combination thereof. The bone structure support is capable of being bent or flexed, capable of being bent repeatedly without breaking or getting damaged, and it is flexible. It is capable of resuming its original shape after stretching or compression; it can be springy; it can bend and snap back readily without breaking, it can be able to flex; it can be able to bend easily. When attempting to turn or twist the bone structure support, it can be pliable without breaking, yielding to pressure; not stiff or brittle.

In accordance with certain embodiments, the sleepy heads neck pillow according to the invention may comprise inner material such as memory foam from a low density to a high density, shredded memory foam from a low density to a high density, polyester foam from a low density to a high density, polyester fibers, any type of feathers, cotton, beads, micro beads, gel/foam, PU foam from a low density to a high density, a mixture thereof, for example: 50% of cotton and 50% of polyester fibers or any other material/foam used for pillows inside the pillow.

In accordance with certain embodiments, the Bone Structure is U-shaped or C-shaped or O-shaped.

Until now, no one has invented a head and neck pillow, which is out on the market today, like the present invention.

In accordance with certain embodiments, the sleepy head and neck pillow of the present invention has four or more different uses. It allows the wearer to sleep while sitting up during transportation (airplane, train, bus, car, etc.). It gives support to people who have neck injuries, during transportation (airplane, train, bus, car, etc.). While not using the clip/strap system, it can be used as a comfortable resting pillow. One of other uses is the lower back use, which is a use to give support to the lower back, hips, butt and spine.

The sleepy head and neck pillow of the invention will be useful to insurance companies because it will provide their customers with extra safety which will reduce the risk of neck injuries, therefore saving money for the insurance companies, and their customers. Whiplash victims can also use the sleepy head and neck pillow of the invention to ease their pain because it will give their neck support and comfort. Airline companies can also build sleepy head and neck pillow of the invention into the airplane seats so that the passengers will be able to sleep sitting up during flight with great comfort. The airline companies can also rent sleepy head and neck pillow of the invention on their flights for their passengers.

The second use of the sleepy heads neck pillow of the present invention is a side use. For the side use, the design of the bone structure support and the pillow itself can support both sides of the wearer's head "Left or Right" but not at the same time; it has to be one side or the other because with the side use there is only one side and a back of the pillow. It is designed to fit and contour the head, neck and face shape perfectly. With this side use "Side Sleepy Head" for a neck pillow; the wearer will have a cozy feeling like sleeping in their bed. A lot of people sleep on their side in their bed. Besides the fact that this is a much more natural way to sleep, this new Side Use of "Side Sleepy Head" will keep the head and neck in a prefect position, while sleeping sitting up with great stability and comfort, so that the users won't wake-up each time their head nods forward. There are 3 distinct parts of the Side Use, using the front, the back, and the side. Each part of the pillow can be used to support many different parts. It can support the head, neck, shoulders, face or body. When used as the side use, the back of the pillow (i.e., the neck bone support and the upper back bone support) can be used as the side of the pillow. When used as the side use, the side of the pillow (i.e., the arm bone support) can be used as the front and back of the pillow.

Figure 20:
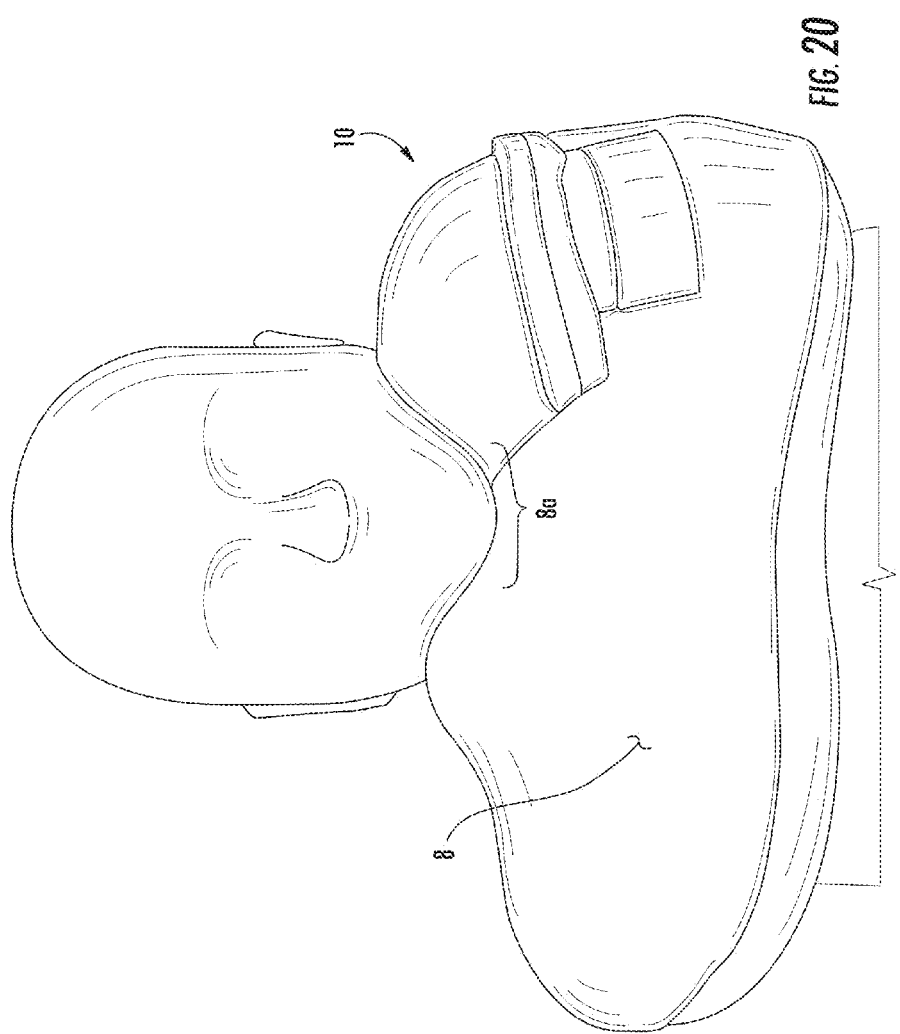
FIG. 20 is a view of the pillow in a first side use in accordance with certain embodiments.
Figure 21:
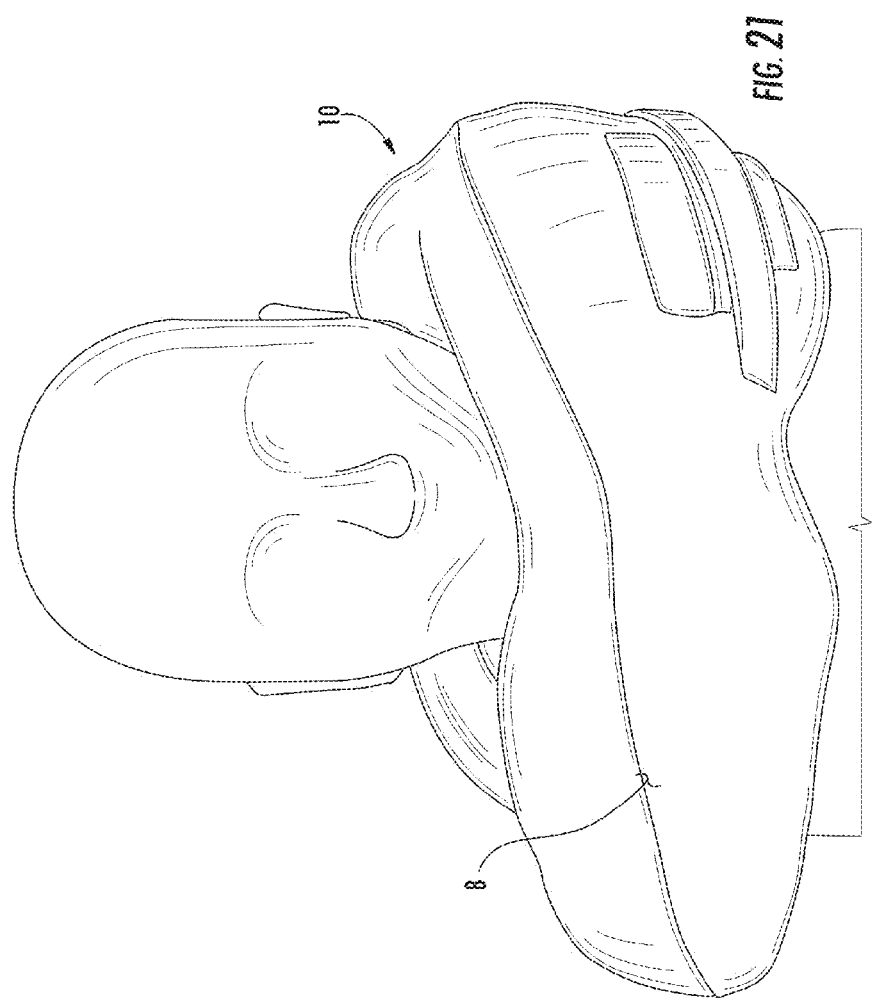
FIG. 21 is a view of the pillow in a second side use in accordance with certain embodiments.
Figure 22:
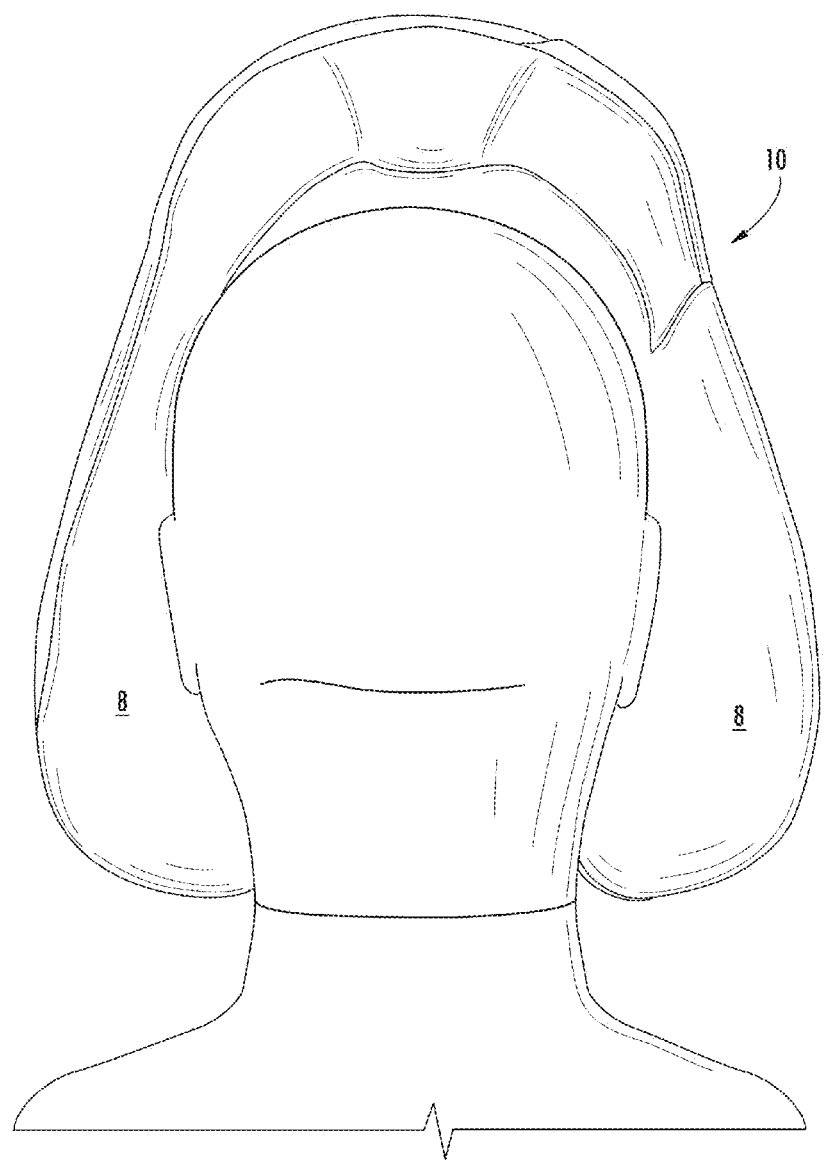
FIG. 22 is a top view of a first face down use of the pillow in accordance with certain embodiments.
Figure 23:
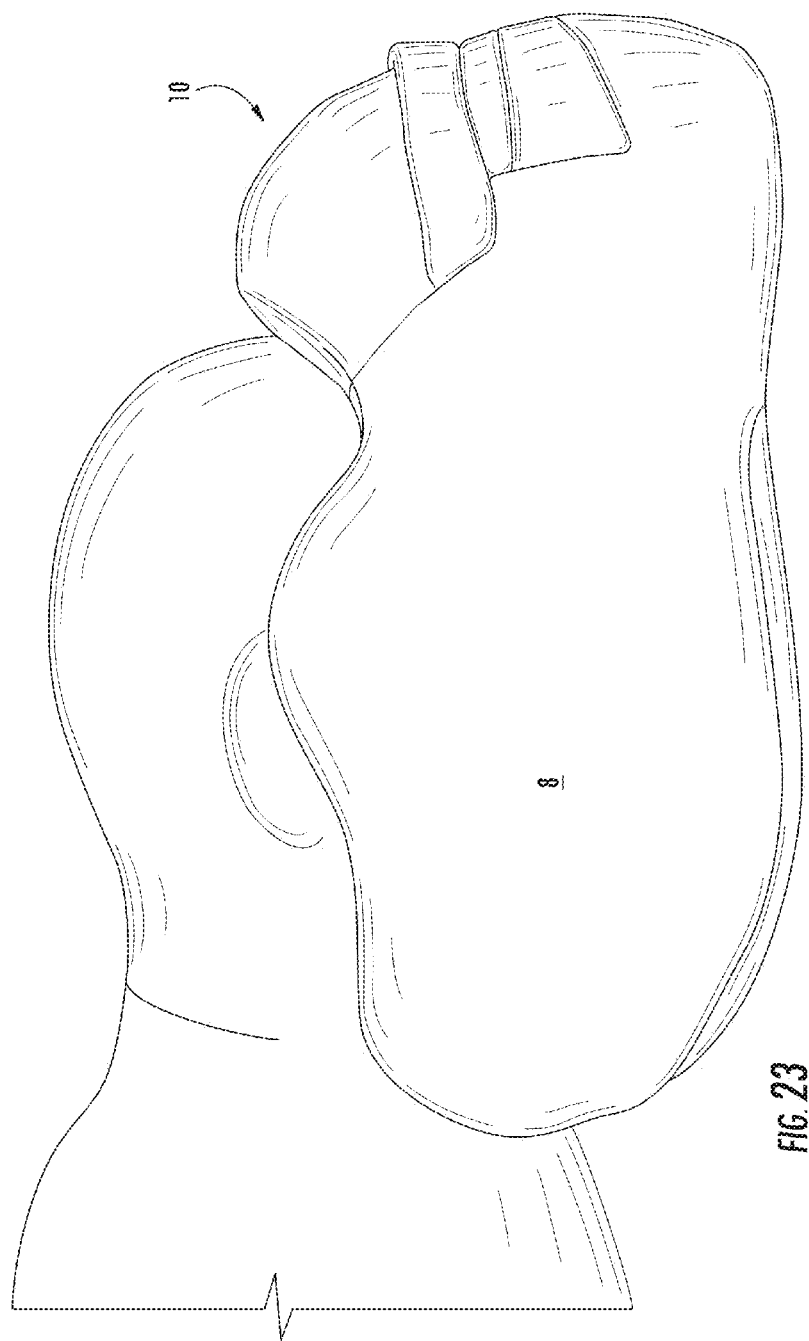
FIG. 23 is a side view of the face down use of the pillow of FIG. 22.

FIG. 20 shows a side use of the sleepy heads neck pillow in accordance with certain embodiments. The pillow is positioned on the wearer such that one of the arm bones 8 supports the wearer's chin as shown. In accordance with certain embodiments, this can be accomplished by positioning the gap defined by the arm bones 8 at the side of a wearer's neck (e.g., about 90° from the wearer's face), and guiding the sleepy heads neck pillow towards the wearer's neck until the neck contacts the back of the pillow (the neck bone support) as shown in FIG. 20. The pillow can then be optionally rotated so that the neck bone support is positioned at the back of the wearer's neck, or the pillow can remain in the unrotated position (the side use position) of FIG. 20. In this regard, at least one of the arm bones 8 can have an arc-shaped contour region at 8a that allows the wearer's chin and/or cheek to rest comfortably on the arm bone 8. FIG. 21 shows another embodiment of the side use, where the pillow is upside-down relative to the position shown in FIG. 20. In this embodiment, most or all of the wearer's neck is positioned in the gap between the two arm bones, and the arc-shaped region is not used to support the chin or cheek of the wearer.

The back of the pillow "originally called the arm bone support" gives a great support and comfort to the neck and head of the user when used as the side use. It contours the cheek and chin of the wearer perfectly for an optimal support and comfort. This way the head of the wearer will not nod forward causing risk of neck injuries.

The side of the pillow originally the back of the pillow which was the neck bone support and the upper back bone support gives an optimal comfort and stability for the side of the head, side of the neck and shoulder of the wearer.

For the shape and design of the pillow, the side part extends to the ear of the wearer, so that it allows a cozy feeling of like being in a bed.

When used as the side use, the pillow can be used on either side of the wearer's shoulders. The pillow is designed to support both sides of the head "left or Right" of the wearer, and designed to perfectly contour the side of the head, neck and face of the wearer. By the side use, the neck can be maintained in a correct position and the head can be kept in the correct position.

Figure 24:
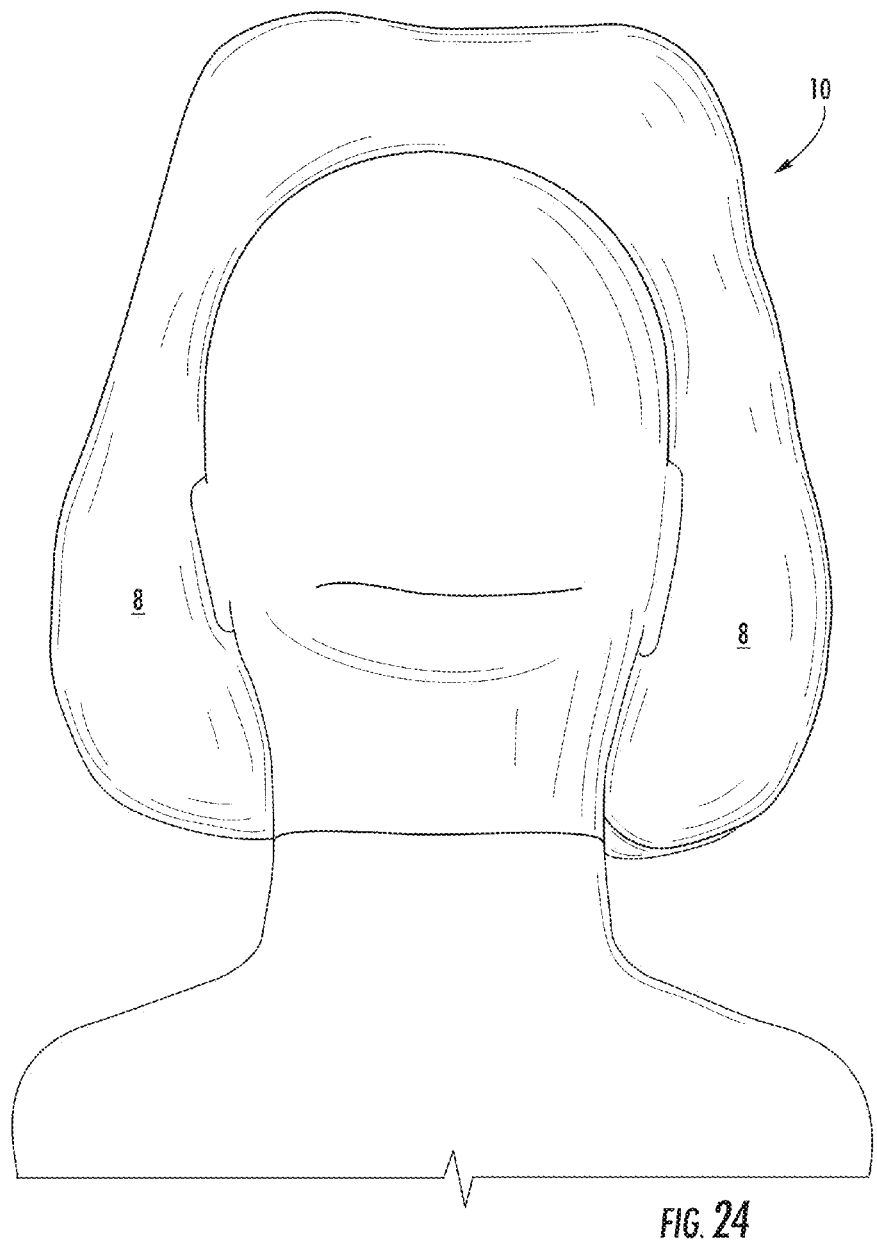
FIG. 24 is a top view of a second face down use of the pillow in accordance with certain embodiments.
Figure 25:
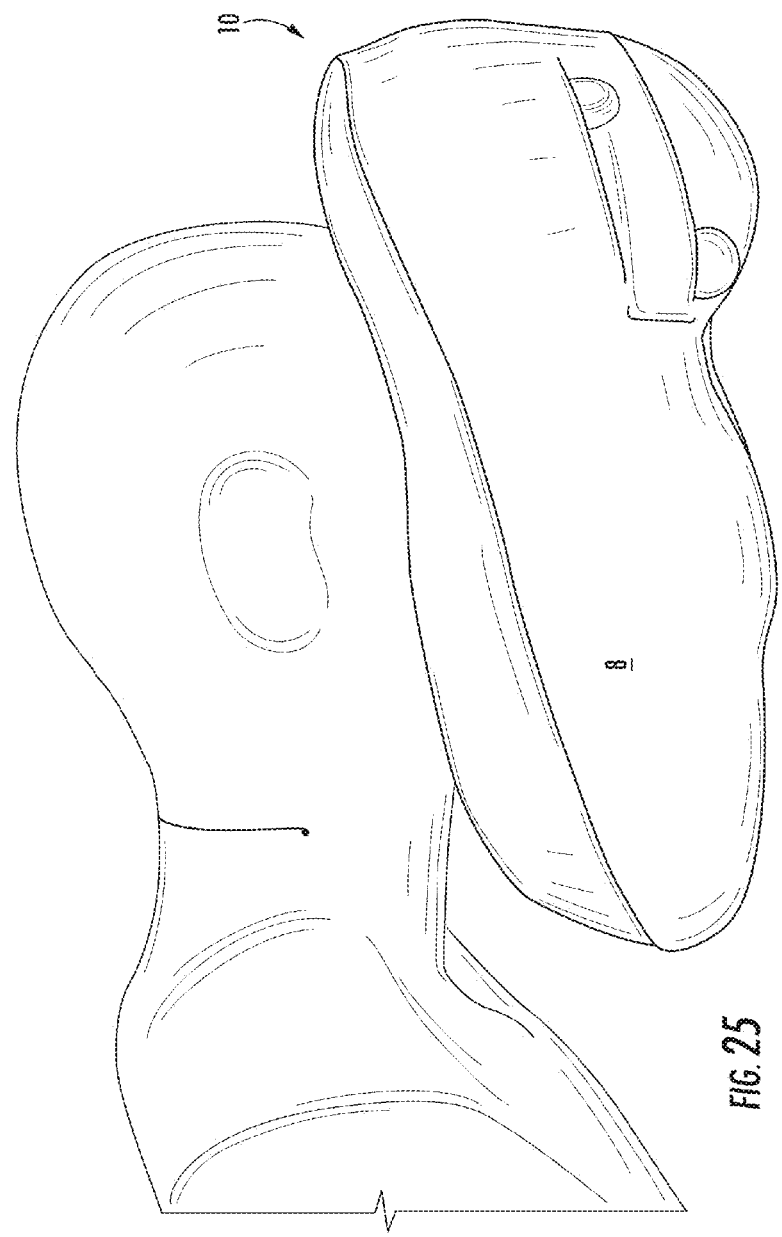
FIG. 25 is a side view of the face down use of the pillow of FIG. 24.

As shown in FIGS. 22-25, another use of the sleepy heads neck pillow of the present invention is a face down use. For the face down use, the pillow can be used, for instance when the user is in the spa massage position. With the face down use, the wearer does not wear the sleepy heads neck pillow on their neck but lays their face down on the pillow. In accordance with certain embodiments, in this use the pillow will be supported on a substrate, such as the floor, a bed or a couch. With this face down use, both sides of the pillow can be used, the top (FIGS. 22 and 23) or the bottom (FIGS. 24 and 25). The user's face is positioned within the gap between the two arm bones 8. The user's face and/or head is thus comfortably surrounded and supported by the arm bones and neck bone as shown. Lying down on the pillow will allow the wearer the great feeling to be like on a spa massage table.

The sleepy heads neck pillow will give to the wearer a great stability and comfort to the head, face and forehead. Due to the inner bone structure the pillow won't be squashed flat.

Because of the specific design of sleepy heads neck pillow and the bone structure support, the wearer's face will always be lifted up, and the wearer will be able to breathe comfortably while sleeping during the spa massage position.

Figure 29:
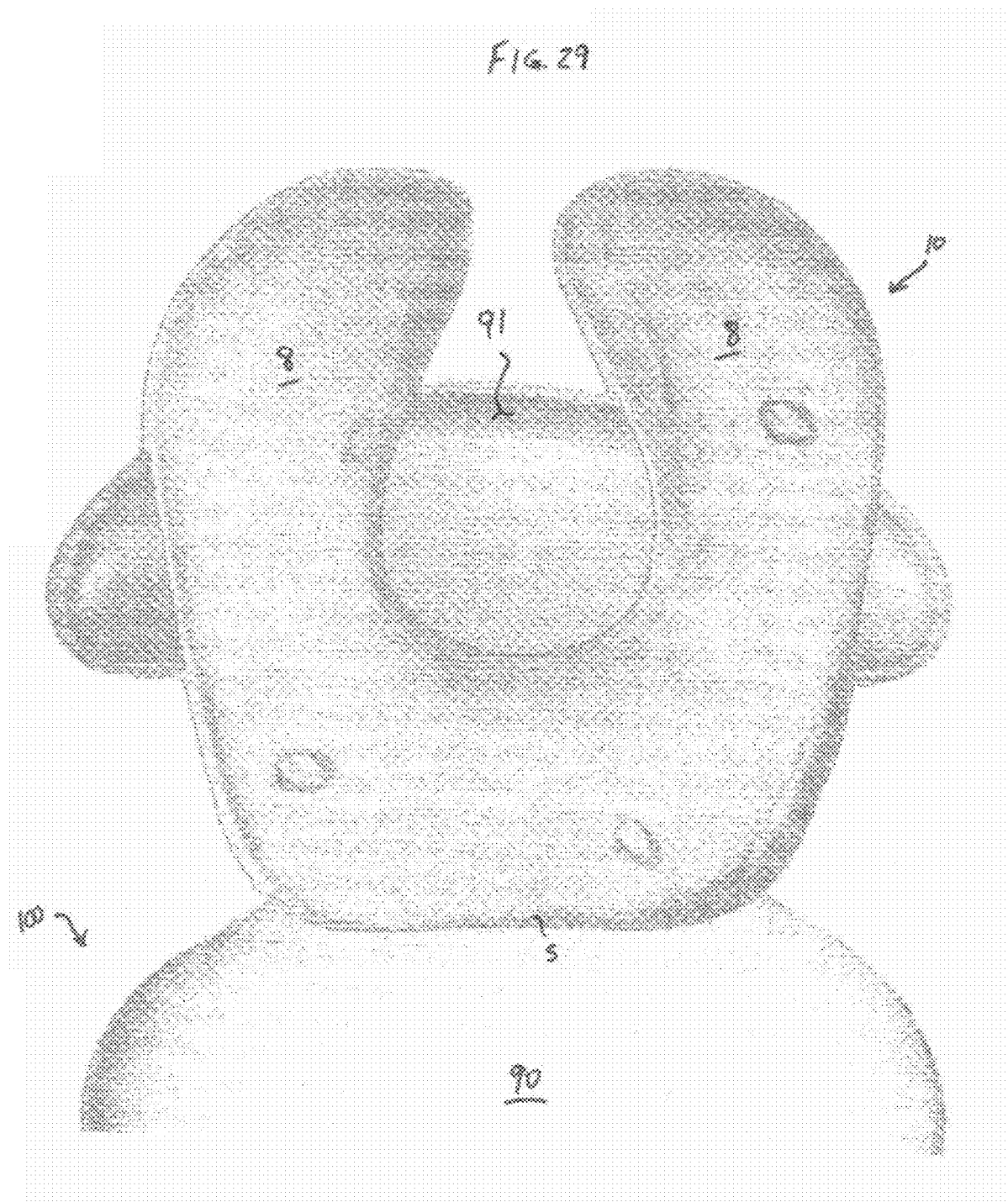
FIG. 29 is a front view of the pillow positioned on a chair in accordance with certain embodiments.
Figure 30:
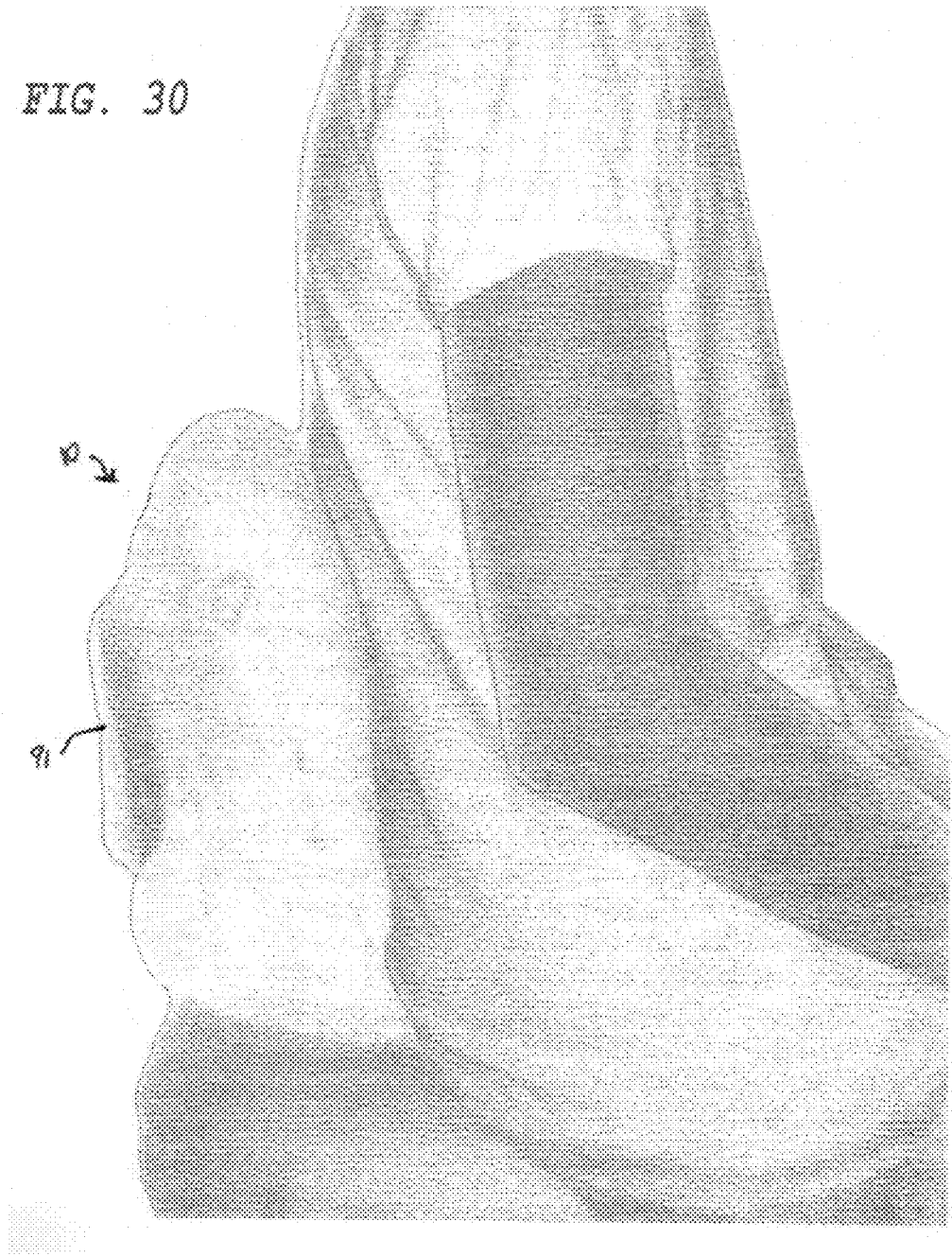
FIG. 30 is a side view showing a user sitting on the chair of FIG. 29 with the pillow providing support to the wearer's lower back, hip, butt and/or spine.

FIGS. 29 and 30 show a further use of the pillow in accordance with certain embodiments. The pillow 10 can be placed with the neck bone 5 (and/or back bone if present) resting on the seat 90 of a chair or stool 100 or the like, and the arm bones extending upwardly from the seat 90 and resting on the seat back 91. The user then sits on the seat 90 and leans back against the pillow 10 as shown in FIG. 30. The pillow 10 is thus positioned between the user's back and the seat back 91, and the arm bones 8 extend upwardly along the sides of the wearer's back, with the gap between the arm bones positioned at or near the middle of the user's back. In this position the pillow provides support for the user's back, especially the lower back, and for the user's spine, hips, and/or butt.

The sleepy head and neck pillow of the invention may be made in six different sizes. X-Small (infant), Small (Child), Medium (Adult), Large (Adult), X-Large and Jumbo which is used for the lower back use. The pillow structure and shape may be exactly the same, only the size may be different.

FULL LISTINGS OF ITEMS

1. Adjustable Seat Clips
2. Adjustable Seat Straps
3. Detachable Clips
4. Supportive Seat Brace
5. Neck Bone Support
6. Supportive Arm Strap
7. Support Belt
8. Arm Bone
8a. Arc shaped region on arm bone
8b. Distal end of arm bone
9. Upper Back Bone Support
10. Pillow
11. Shoulder Support Padding
12. Pillow Cover
50. Diagonal cut
60. Intermediate panel of collapsible system
61. Indentation of collapsible system
70. Top edge of neck bone support
71. Bottom edge of neck bone support
72. Intermediate region of neck bone support
73. Left edge of neck bone support
74. Right edge of neck bone support
80. First point of angle
81. Second point of angle
83. Wave-like contour of arm bone
90. Chair seat
91. Chair back
1. 100. Chair

The invention claimed is:

1. A method of donning a sleepy heads neck pillow on a wearer, said sleepy heads neck pillow comprising a pillow with a bone structure support inside the pillow, wherein the bone structure support is fully incased in the pillow, and the bone structure support comprises two parts; a neck bone support having a top edge, a bottom edge, a left edge and a right edge, wherein the neck bone support is configured to conform to and support the back of the neck of the user, and two or more arm bone supports respectively extending from the left and/or right edges of the neck bone support and defining a gap between them, wherein a length of each arm bone support is substantially greater than a width of each arm bone support so that the arm bone supports are configured to extend forwardly of the shoulders of the user to support the user's head when the head is resting to the side, and, the bone structure support is made of one piece or multiple parts; said method comprising:

positioning said gap at the left side or at the right side of a wearer's neck, and guiding said sleepy heads neck pillow towards the wearer's neck.

2. The method of claim 1, wherein at least one of said arm bone supports comprises an arc-shaped contour, and wherein said pillow is guided towards the wearer's neck such that the chin of the wearer rests in said arc-shaped contour of said arm bone support.

3. The method of claim 1, further comprising rotating said sleepy heads neck pillow such that said neck bone support is positioned at the back of the wearer's neck.

4. The method of claim 1, wherein said sleepy heads neck pillow further comprises an upper back bone support that is extended down at an angle from the bottom edge of the neck bone support so that the upper back bone support is configured to give extra support to the neck and upper back of the user, and wherein said step of rotating said sleepy heads neck pillow causes said upper back bone support to be positioned on one of the wearer's shoulders.

* * * * *